United States Patent
Scott

(10) Patent No.: US 6,495,683 B2
(45) Date of Patent: Dec. 17, 2002

(54) 4-OXO-4,7-DIHYDRO-THIENO[2,3-B] PYRIDINE-5-CARBOXAMIDES AS ANTIVIRAL AGENTS

(75) Inventor: Allen Scott, Kalamazoo, MI (US)

(73) Assignee: Pharmacia and Upjohn Company, Kalamazoo, MI (US)

(*) Notice: Subject to any disclaimer, the term of this patent is extended or adjusted under 35 U.S.C. 154(b) by 0 days.

(21) Appl. No.: 09/824,334

(22) Filed: Apr. 2, 2001

(65) Prior Publication Data

US 2002/0006937 A1 Jan. 17, 2002

Related U.S. Application Data

(62) Division of application No. 09/521,027, filed on Mar. 7, 2000, now Pat. No. 6,239,142.
(60) Provisional application No. 60/123,660, filed on Mar. 9, 1999.

(51) Int. Cl.[7] .................. C07D 333/36; C07D 409/06; C07D 495/04
(52) U.S. Cl. ..................... 544/127; 544/146; 549/68
(58) Field of Search ............... 549/68; 544/127, 544/146

(56) References Cited

U.S. PATENT DOCUMENTS

| | | | |
|---|---|---|---|
| 4,125,611 A | 11/1978 | Yamade et al. ............ 424/246 |
| 4,145,418 A | 3/1979 | Kuwada et al. ............ 424/246 |
| 4,559,157 A | 12/1985 | Smith et al. ............... 252/90 |
| 4,568,649 A | 2/1986 | Bertoglio-Matte .......... 436/534 |
| 4,608,392 A | 8/1986 | Jacquet et al. ............. 514/844 |
| 4,767,766 A | 8/1988 | Baker et al. ............... 514/301 |
| 4,820,508 A | 4/1989 | Wortzman ................. 424/59 |
| 4,938,949 A | 7/1990 | Borch et al. ............... 424/10 |
| 4,959,363 A | 9/1990 | Wentland ................ 514/235.2 |
| 4,992,478 A | 2/1991 | Geria ..................... 514/782 |
| 5,593,943 A | 1/1997 | Nuebling et al. ........... 504/221 |
| 5,817,819 A | 10/1998 | Furuya et al. ............. 546/114 |

FOREIGN PATENT DOCUMENTS

| | | | |
|---|---|---|---|
| DE | 4227747 | 2/1994 | ......... C07D/487/04 |
| EP | 0443568 | 2/1991 | |
| EP | 0443568 A1 | 8/1991 | ......... C07D/495/04 |
| EP | 505058 | 9/1992 | ......... C07D/495/04 |
| JP | 07076586 A | 3/1995 | ....... C07D/491/048 |
| JP | 08301849 A | 11/1996 | ......... C07D/217/26 |
| JP | 9208496 | 8/1997 | ......... A61K/47/40 |
| WO | 92/03427 | 3/1992 | ......... C07D/307/82 |
| WO | 95/28405 | 10/1995 | ......... C07D/495/04 |
| WO | 96/18616 | 6/1996 | ......... C07D/213/75 |
| WO | 96/18617 | 6/1996 | ......... C07D/213/75 |
| WO | 97/40846 | 11/1997 | ......... A61K/38/09 |
| WO | 98/11073 | 3/1998 | ......... C07D/215/48 |
| WO | 99/62908 | 12/1999 | ......... C07D/495/04 |

OTHER PUBLICATIONS

Chemical Abstracts, vol. 85:46627 (1976),; Abstract of DE2447477, Apr. 1976.*

Cook, N.D., et al., *Pharmaceutical Manufacturing International*, pp. 49–53, (1992).

El–Abadelah, M.M., et al., "Synthesis and Chiroptical Properties of Some N–(2–Chloro–7–cyclopropyl–4.7–dihydro–4–oxo–thieno[2,3–b]pyridine–5–carbonyl) L–a–Amino Esters", *Zeitschrift fur Naturforschung B, A Journal of Chemical Sciences*, 52 (3), pp. 419–426, (1997).

Martin, E.W., *Remington's Pharmaceutical Sciences, 15th Edition*, Mark Publishing Company, (1975).

Takeuchi, K., "Scintillation Proximity Assay", *Laboratory Practice*, 41 (9), pp. 11–13, (Sep. 1992).

* cited by examiner

*Primary Examiner*—Bernard Dentz
(74) *Attorney, Agent, or Firm*—Schwegman, Lundberg, Woessner & Kluth, P.A.

(57) ABSTRACT

The invention provides a compound of formula I:

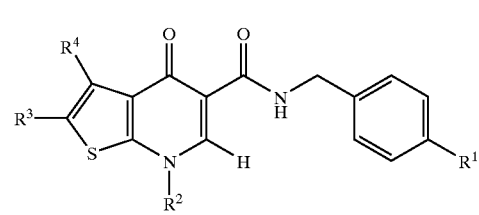

wherein $R^1$, $R^2$, $R^3$, and $R^4$ have any of the values defined in the specification, or a pharmaceutically acceptable salt thereof, as well as processes and intermediates useful for preparing such compounds or salts, and methods of preventing or treating a herpesvirus infection using such compounds or salts.

8 Claims, No Drawings

4-OXO-4,7-DIHYDRO-THIENO[2,3-B] PYRIDINE-5-CARBOXAMIDES AS ANTIVIRAL AGENTS

PRIORITY OF INVENTION

This application is a Divisional of U.S. application Ser. No. 09/521,027 filed Mar. 7, 2000, now U.S. Pat. No. 6,239,142, which claims priority of invention under 35 U.S.C. §119(e) from U.S. Provisional Application Number 60/123660 filed on Mar. 9, 1999.

FIELD OF THE INVENTION

The present invention provides 4-oxo4,7-dihydro-thieno [2,3-b]pyridine-5-carboxamide derivatives, more specifically, 5-benzylaminocarbonyl4-oxo-4,7-dihydro-thieno[2,3-b]pyridine derivatives of formula (I), which are useful as antiviral agents (e.g. as agents against viruses of the herpes family).

BACKGROUND OF THE INVENTION

The herpesviruses comprise a large family of double stranded DNA viruses. They are also a source of the most common viral illnesses in man. Eight of the aherpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immunocompromised patients such as retinitis, pneumonia, and gastrointestinal disease. VZV is the causative agent of chicken pox and shingles. EBV causes infectious mononucleosis. It can also cause lymphomas in immunocompromised patients and has been associated with Burkitt's lymphoma, nasopharyngeal carcinoma, and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Kaposi's sarcoma, body cavity based lymphomas, and multiple myeloma.

SUMMARY OF THE INVENTION

Applicant has discovered compounds that are useful as antiviral agents for treating herpesviral infections. Accordingly, the invention provides a compound of

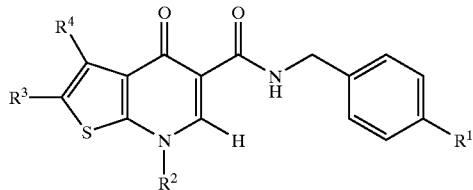

I or a pharmaceutically acceptable salt thereof wherein, $R^1$ is
(a) Cl,
(b) Br,
(c) CN,
(d) $NO_2$, or
(e) F;

$R^2$ is
(a) H,
(b) $R^5$,
(c) $NR^7R^8$,
(d) $SO_2R^9$, or
(e) $OR^9$;

$R^3$ is
(a) H,
(b) halo,
(c) aryl,
(d) $S(O)_mR^6$,
(e) $(C=O)R^6$,
(f) $(C=O)OR^9$,
(g) cyano,
(h) het, wherein said het is bound via a carbon atom,
(i) $OR^{10}$,
(j) Ohet,
(k) $NR^7R^8$
(l) $SR^{10}$,
(m) Shet,
(n) $NHCOR^{12}$,
(o) $NHSO_2R^{12}$, or
(p) $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$alkyl, and $SO_mR^9$;

$R^4$ is
(a) H,
(b) halo,
(c) $C_{1-4}$alkyl, or
(d) $R^4$ together with $R^3$ form a carbocyclic or het, either of which may be optionally substituted by $NR^7R^8$, by $C_{1-7}$alkyl which may be optionally substituted by $OR^{14}$, or by het, wherein said het is bound via a carbon atom;

$R^5$ is
(a) $(CH_2CH_2O)_iR^{10}$,
(b) het, wherein said het is bound via a carbon atom,
(c) aryl,
(d) $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl which may be further substituted by het, $OR^{10}$, or $NR^7R^8$, or
(e) $C_{3-8}$cycloalkyl which may be partially unsaturated and optionally substituted by one or more substituents selected from a group consisting of $R^{11}$, $NR^7R^8$, $SO_mR^9$, and $C_{1-7}$alkyl optionally substituted by $R^{11}$, $NR^7R^8$, or $SO_mR^9$;

$R^6$ is
(a) $C_{1-7}$alkyl,
(b) $NR^7R^8$,
(c) aryl, or
(d) het, wherein said het is bound via a carbon atom;

$R^7$ and $R^8$ are independently
(a) H,
(b) aryl,
(c) $C_{1-7}$alkyl which may be partially unsaturated and is optionally substituted by one or more substituents selected from a group consisting of $NR^{10}R^{10}$, $R^{11}$, $SO_mR^9$, $CONR^{10}R^{10}$, and halo, or,
(d) $R^7$ and $R^8$ together with the nitrogen to which they are attached form a het;

$R^9$ is
- (a) aryl,
- (b) het,
- (c) $C_{3-8}$cycloalkyl, or
- (d) $C_{1-7}$alkyl which may be partially unsaturated and is optionally substituted by one or more substituents selected from a group consisting of $NR^{10}R^{10}$, $R^{11}$, SH, $CONR^{10}R^{10}$, and halo;

$R^{10}$ is
- (a) H, or
- (b) $C_{1-7}$alkyl optionally substituted by OH;

$R^{11}$ is
- (a) $OR^{10}$,
- (b) Ohet,
- (c) Oaryl,
- (d) $CO_2R^{10}$,
- (e) het,
- (f) aryl, or
- (g) CN;

$R^{12}$ is
- (a) H,
- (b) het,
- (c) aryl,
- (d) $C_{3-8}$cycloalkyl, or
- (e) $C_{1-7}$alkyl optionally substituted by $NR^7R^8$ or $R^{11}$;

$R^{13}$ is
- (a) $(P=O)(OR^{14})_2$,
- (b) $CO(CH_2)_nCON(CH_3)-(CH_2)_nSO_3^-M^+$,
- (c) an amino acid,
- (d) C(=O)aryl, or
- (e) C(=O)$C_{1-7}$alkyl optionally substituted by $NR^7R^8$, aryl, het, $CO_2H$, or $O(CH_2)_nCO_2R^{14}$);

$R^{14}$ is
- (a) H, or
- (b) $C_{1-7}$alkyl;

each i is independently 2, 3, or 4;

each n is independently 1, 2, 3, 4 or 5;

each m is independently 0, 1, or 2;

M is sodium, potassium, or lithium;

wherein any aryl is optionally substituted with one or more substituents selected from the group consisting of halo, OH, cyano, $CO_2R^{14}$, $CF_3$, $C_{1-6}$alkoxy, and $C_{1-6}$alkyl which maybe further substituted by one to three $SR^{14}$, $NR^{14}R^{14}$, $OR^{14}$, het, or $CO_2R^{14}$; and wherein any het is optionally substituted with one or more substituents selected from the group consisting of halo, OH, cyano, phenyl, $CO_2R^{14}$, $CF_3$, $C_{1-6}$alkoxy, oxo, oxime, and $C_{1-6}$alkyl which maybe further substituted by one to three $SR^{14}$, $NR^{14}R^{14}$, $OR^{14}$, or $CO_2R^{14}$.

In another aspect, the present invention also provides:

a pharmaceutical composition comprising a compound of formula I, or a pharmaceutically acceptable salt thereof, and a pharmaceutically acceptable excipient (the composition preferably comprises an effective antiviral amount of the compound or salt);

a method of treating or preventing a herpesviral infection, comprising administering to a mammal (e.g. a human) in need of such treatment, a compound of formula (I) or a pharmaceutically acceptable salt thereof; and a method for inhibiting a viral DNA polymerase, comprising contacting (in vitro or in vivo) the polymerase with an effective inhibitory amount of a compound of formula I, or a pharmaceutically acceptable salt thereof.

The invention also provides novel intermediates and processes disclosed herein that are useful for preparing compounds of formula L.

Compounds of formula I have a 4-substituted benzylaminocarbonyl substituent at the 5-position of the thieno[2,3-b]pyridine ring system. This substitution pattern has been found to provide compounds with significantly improved antiviral activity compared to thienopyridines lacking this substitution.

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Het is a four- (4), five- (5), six- (6), or seven- (7) membered saturated or unsaturated heterocyclic ring having 1, 2, 3, or 4 heteroatoms selected from the group consisting of oxy, thio, sulfinyl, sulfonyl, and nitrogen, which is optionally fused to a benzene ring, or any bicyclic heterocycle group. Het includes "heteroaryl," which encompasses a radical attached via a ring carbon of a monocyclic aromatic ring containing five or six ring atoms consisting of carbon and 1, 2, 3, or 4 heteroatoms each selected from the group consisting of non-peroxide oxy, thio, and N(X) wherein X is absent or is H, O, $C_{1-4}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

When $R^4$ together with $R^3$ form a carbocyclic, $R^4$ and $R^3$ together can be a 3, 4, 5, or 6 membered saturated or unsaturated carbon chain.

"Amino acid," includes a residue of natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, a-methyl-alanine, para-benzoylphenylalanine, phenylglycine, propargylglycine, sarcosine, and tert-butylglycine). An amino acid can conveniently be linked to the remainder of a compound of formula I through the carboxy terminus, the amino terminus, or through any other convenient point of attachment, such as, for example, through the sulfur of cysteine. In particular, an amino acid can conveniently be linked to the remainder of a compound of formula I through the carboxy terminus.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. In particular, it is understood that compounds of formula I wherein $R^2$ is hydrogen can exist in the corresponding tautomeric "enol" form, and that such tautomers are included as compounds of the invention.

The carbon atom content of various hydrocarbon-containing moieties is indicated by a prefix designating a lower and upper number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, $C_{1-7}$alkyl can be methyl, ethyl, propyl, isopropyl, butyl, iso-butyl, sec-butyl, pentyl, 3-pentyl, hexyl, or heptyl; $C_{3-8}$cycloalkyl can be cyclopropyl, cyclobutyl, cyclopentyl, cyclohexyl, cycloheptyl, or cyclooctyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C(=O)C_{1-7}$alkyl can be acetyl, propanoyl, butanoyl, pentanoyl, 4-methylpentanoyl, hexanoyl, or heptanoyl; aryl can be phenyl, indenyl, or naphthyl; het can be pyrrolidinyl, piperidinyl, morpholinyl, thiomorpholinyl, or heteroaryl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for Het is a five- (5), six- (6), or seven- (7) membered saturated or unsaturated ring containing 1, 2, 3, or 4 heteroatoms selected from the group consisting of non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic het diradical thereto.

A specific value for $R^1$ is F, Cl, or Br.

A more specific value for $R^1$ is Cl.

A specific value for $R^2$ is H.

A specific value for $R^2$ is $R^5$, $NR^7R^8$, $SO_2R^9$, or $OR^9$.

A specific value for $R^2$ is $R^5$.

A more specific value for $R^2$ is methyl, ethyl, propyl, isopropyl, butyl, tert-butyl, carboxymethyl, ($C_{1-7}$ alkoxy) carbonylmethyl, 2-hydroxyethyl, 2-(2-methoxy-ethoxy) ethyl, 3-(2-tetrahydropyranyloxy)propyl, 2-morpholinoethyl, 2-(diethylamino)ethyl, 2-(dimethylamino)ethyl, 2-piperidinoethyl, 3-piperidinopropyl, 2-(1-methylpyrrolidin-2-yl)ethyl, 2-(diisopropylamino)ethyl, 2-pyrrolidin-1-ylethyl, 3-(dimethylamino)propyl, benzyl, 3-fluorobenzyl, 3-phenylpropyl, 2-tetrahydrofuranylmethyl, 2-pyrrolidinoethyl, 3-pyridylmethyl, or vinyl.

A more specific value for $R^2$ is methyl, ethyl, isopropyl, 2-hydroxyethyl, 2-(diethylamino)ethyl, or 2-(dimethylamino)ethyl.

A specific value for $R^3$ is H, halo, $S(O)_mR^6$, $(C=O)R^6$, $(C=O)OR^9$, cyano, or $C_{1-7}$alkyl which may be partially unsaturated and optionally substituted by one or more substituents of the group $R^{11}$, $OR^{13}$ $SR^{10}$, $SR^{13}$, $NR^7R^8$, halo, $(C=O)C_{1-7}$alkyl, and $SO_mR^9$.

A specific value for $R^3$ is $C_{1-7}$alkyl which may be partially unsaturated and optionally substituted by one or more substituents of the group $R^{11}$, $OR^{13}$, $SR^{10}$, $SR^{13}$, $NR^7R^8$, halo, $(C=O)C_{1-7}$ alkyl, and $SO_mR^9$.

A specific value for $R^3$ is $C_{1-7}$alkyl which may be partially unsaturated and is substituted by one or more substituents of the group $R^{11}$, $OR^{13}$, $SR^{10}$, $SR^{13}$, $NR^7R^8$, halo, $(C=O)C_{1-7}$ alkyl, and $SO_mR^9$.

A specific value for $R^3$ is $C_{1-7}$alkyl which may be partially unsaturated and is substituted by one or more substituents of the group $OR^{10}$, het and $NR^7R^8$.

A specific value for $R^3$ is (Z or E)—CH=CH(CH$_2$)$_n$R$_a$ or —C≡C(CH$_2$)$_n$R$_a$ wherein R$_a$ is $R^{11}$, $OR^{13}$, $SR^{10}$, $SR^{13}$, $NR^7R^8$, halo, $(C=O)C_{1-7}$alkyl, or $SO_mR^9$.

A more specific value for $R^3$ is bromo, iodo, 3-hydroxy-1-propynyl, 3-methoxy-1-propynyl, 4-hydroxy-1-butynyl, 3-hydroxypropyl, cyano, 4,4-di(methoxycarbonyl)-1-butynyl, 4-hydroxybutyl, 3-(3-carboxypropanoyloxy)-1-propynyl, 3-(morpholinoacetoxy)-1-propynyl, 3-(2-amino-3-methylbutanoyloxy)-1-propynyl, thiomorpholinomethyl, N-[2-(4-hydroxyphenyl)-2-hydroxyethyl]-N-(methyl) aminomethyl, morpholinocarbonyl, or 3-[3-(morpholinomethyl)benzoyloxy]-1-propynyl.

A more specific value for $R^3$ is iodo, 3-hydroxy-1-propynyl, 4-hydroxy-1-butynyl, 3-hydroxypropyl, morpholinomethyl, N-[2-(4-hydroxyphenyl)-2-hydroxyethyl]-N-(methyl)aminomethyl or 4-hydroxybutyl.

A specific value for $R^3$ is 3-hydroxy-1-propynyl, morpholinomethyl, N-[2-(4-hydroxyphenyl)-2-hydroxyethyl]-N-(methyl)aminomethyl or 3-hydroxypropyl.

A specific value for $R^5$ is $(CH_2CH_2O)_iR^{10}$.

A specific value for $R^5$ is $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl, which may be further substituted by het, $OR^{10}$, or $NR^7R^8$; wherein $R^9$ and $R^{10}$ have any of the values defined herein; and wherein $R^7$ and $R^8$ are independently (a) H, (b) aryl, or (c) $C_{1-7}$alkyl which may be partially unsaturated and is optionally substituted by one or more substituents selected from a group consisting of $NR^{10}R^{10}$, $R^{11}$, $SO_mR^9$, $CONR^{10}R^{10}$, or halo; and, $R^{11}$ is
(a) $OR^{10}$,
(b) Ohet,
(c) Oaryl,
(d) $CO_2R^{10}$, or
(e) CN.

A specific value for $R^5$ is $C_{1-7}$alkyl which may be partially unsaturated and is optionally substituted by one or more substituents selected from a group consisting of $NR^7R^8$, $R^{11}$, $SO_mR^9$, and $OC_{2-4}$alkyl, which may be further substituted by het, $OR^{10}$, or $NR^7R^8$.

A specific value for $R^5$ is $C_{1-7}$alkyl, which may be partially unsaturated and is optionally substituted by one or more aryl or het.

A more specific value for $R^5$ is $C_{1-7}$alkyl.

A specific compound of formula I is a compound wherein any aryl, or het is optionally substituted with one or two substituents selected from the group consisting of halo, cyano, het, trifluoromethyl, trifluoromethoxy, hydroxy $C_{1-7}$alkoxy, and $C_{1-7}$alkyl; or a pharmaceutically acceptable salt thereof.

Preferred compounds of formula I exclude compounds disclosed specifically or generically in the references cited herein. A preferred compound of formula I excludes a compound of formula I wherein $R^1$ is halo when $R^2$ is hydrogen. Such excluded compounds of formula I can be included in the pharmaceutical compositions and methods described herein or can be excluded therefrom.

The following Charts A–L describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts, by procedures analogous thereto, or by procedures which are known to one of ordinary skill in organic chemistry. All of the variables used in the charts are as defined below or as in the claims.

Chart A.

Optionally substituted 2-aminothiophenes of the formula A-1 are prepared via reduction of the corresponding nitro compounds A-2. Compounds of the formula A-1 are then heated with diethylethoxymethylene malonate followed by thermolysis in diphenyl ether to yield esters of the formula A-4. The esters are converted to amides of the formula A-6 via direct aminolysis with an optionally substituted benzylamine at 190° C. or via hydrolysis to acids of the formula A-5 followed by treatment with carbonyldiimidazole and the amine. Compounds of the formula A-6 are treated with an optionally substituted alkyl halide in the presence of potassium carbonate to yield N-alkylated amides of the formula A-7.

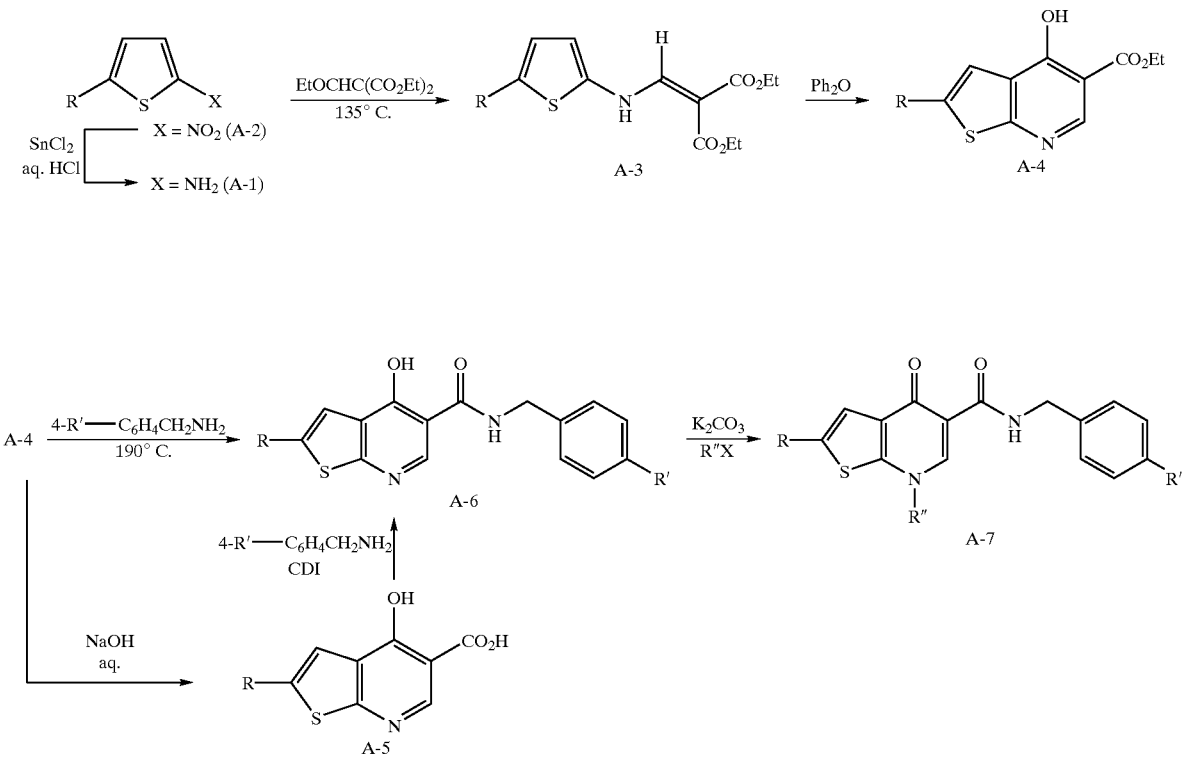

Chart B.

Compound B-1 (5-nitro-2-thiophenesulfonyl chloride) is treated with an amine to yield nitro compounds of the formula B-2. Compounds of the formula B-2 are transformed as in Chart A to yield amides analogous to A-6 and A-7.

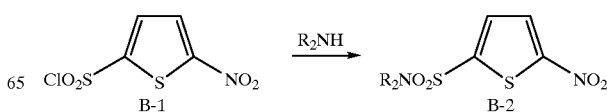

Chart C.

Compounds of the formula C-1 where R is H or alkyl are halogenated to yield compounds of the formula C-2. Compounds of the formula C-2 are transformed as in Chart A to yield amides analogous to A-6 and A-7.

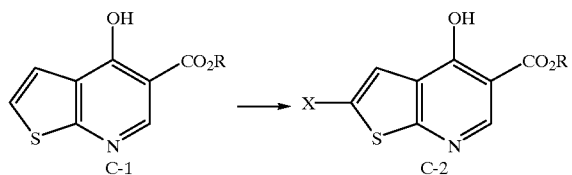

Chart D.

Palladium and copper mediated coupling of D-1 (where X=Br or I) with an alkyne leads to compounds of the formula D-2. Compounds of the formula D-2 are hydrogenated using palladium on carbon as the catalyst to yield the saturated compounds D-4. Compounds D-2 and D-4 are treated with an optionally substituted alkyl halide to yield N-alkylated compounds D-3 and D-5.

Chart E.

Compound E-1 is treated with copper (I) cyanide to yield the cyano compound E-2.

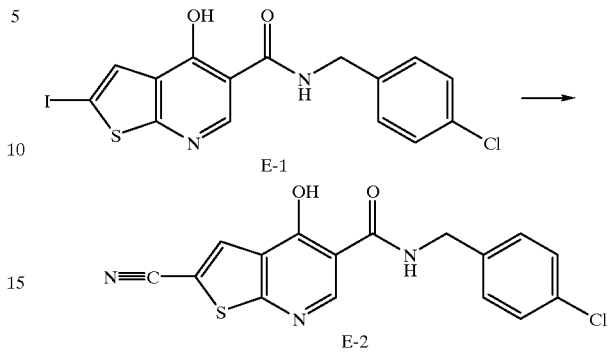

Chart F.

Compounds of the formula F-1 are treated with an optionally substituted alkyl halide in the presence of potassium carbonate to yield N-alkylated esters of the formula F-2. The esters are converted to amides of the formula A-7 via direct aminolysis with a substituted benzylamine or via hydrolysis to acids of the formula F-3 followed by treatment with carbonyldiimidazole and the amine.

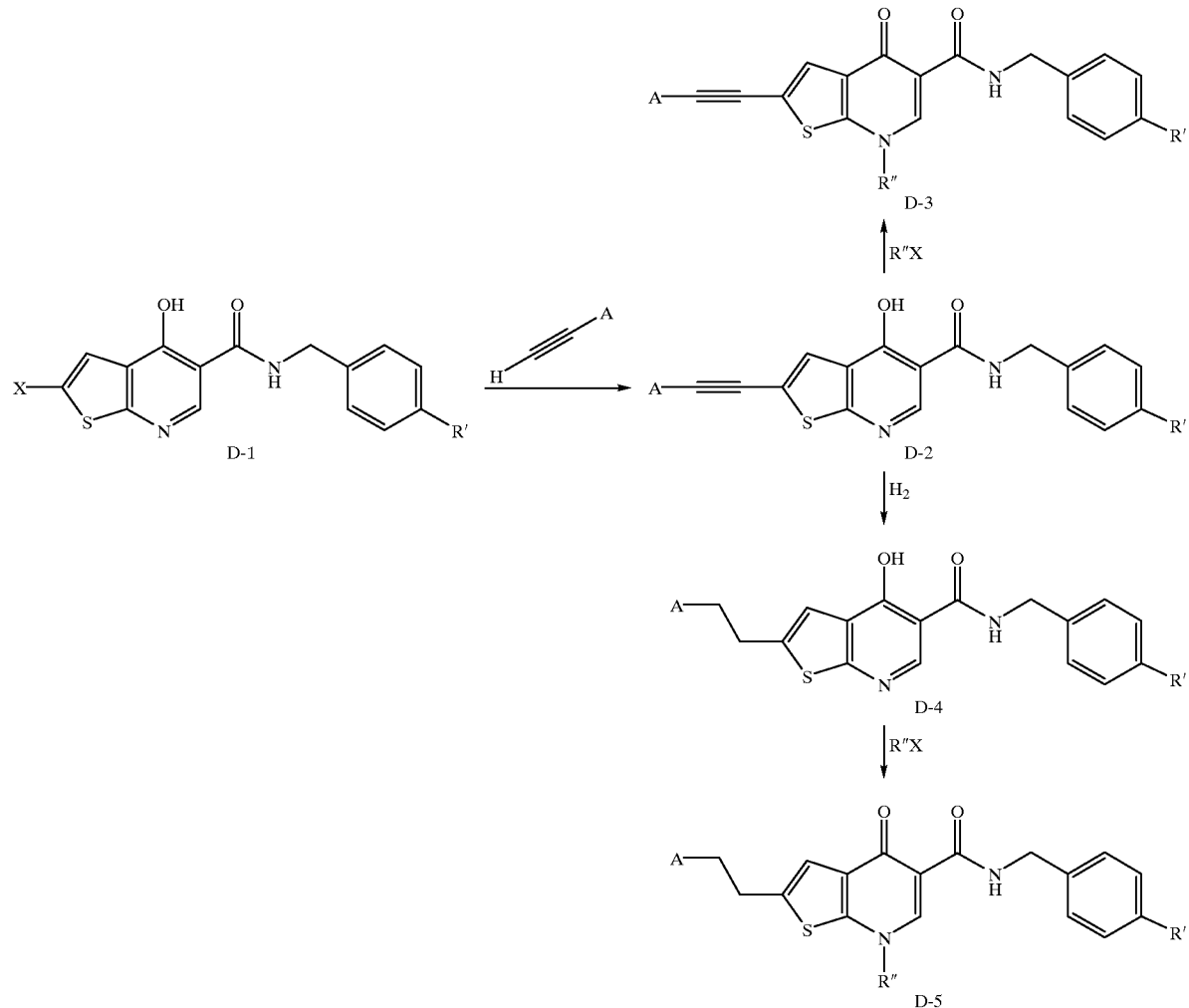

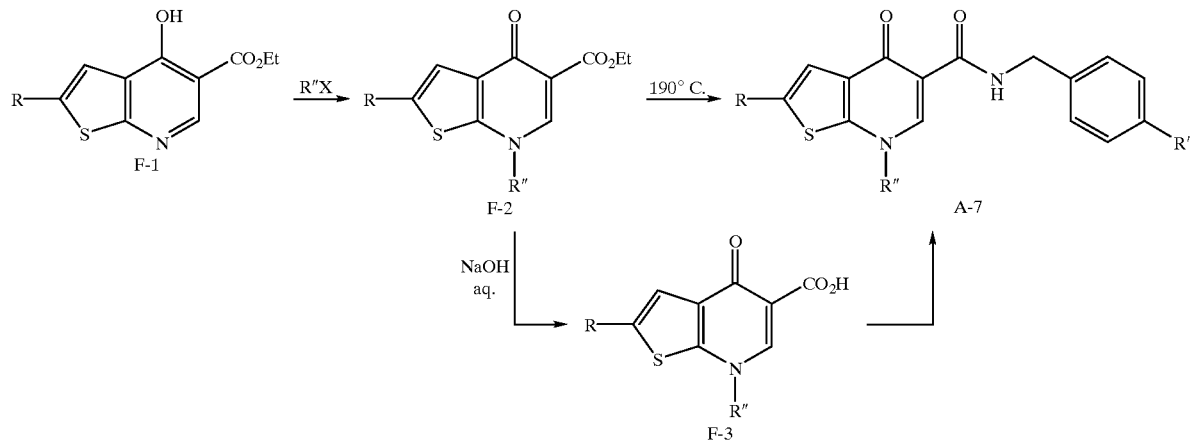

Chart G.

Palladium and copper mediated coupling of G-1 (where R=Br or I) with an alkyne leads to compounds of the formula D-3. Compounds D-3 are hydrogenated using palladium on carbon as the catalyst to yield saturated compounds of the formula D-5.

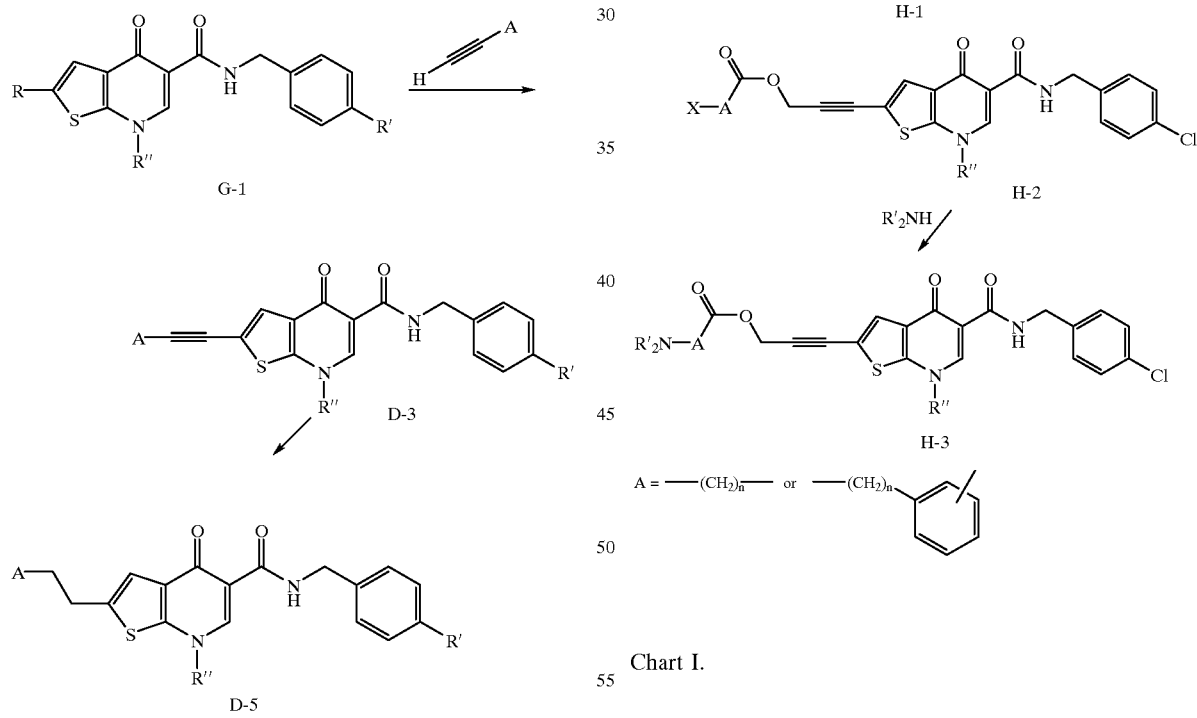

Chart H.

Compounds of the formula H-1 are treated with an acylating agent to yield compounds of the formula H-2 where A is either an alkyl or arylalkyl substituent and X is a halogen (Br, Cl, or I). The halide is then displaced by an amine to yield compounds of the formula H-3.

Chart I.

Compounds of formula I-4 bearing 2-alkylamino substitution are prepared by palladium catalyzed carboxylation of 2-iodothienopyridine E-1 to afford the corresponding 2-methylester I-1. Reduction of I-1 with $LiAlH_4$ affords 2-hydroxymethyl derivative I-2 which may then be treated with an optionally substituted alkyl halide in the presence of potassium carbonate to yield N-alkylpyridones of the formula I-3. Activation of the alcohol with methanesulfonyl chloride followed by displacement with a primary or secondary amine provides compounds of formula I-4.

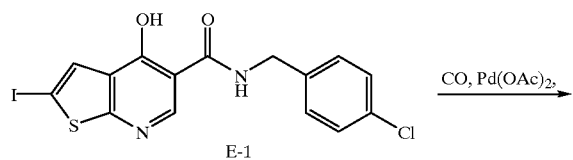

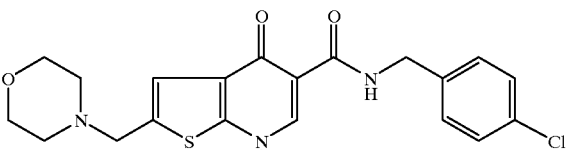

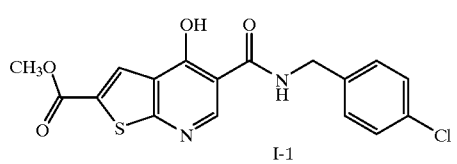

Chart K.

2-Iodothienopyridine-5-carboxamide E-1 undergoes palladium catalyzed carbon monoxide insertion with trapping by an amine to afford 2-carboxamides of the general formula K-1. Compounds K-1 are then treated with an optionally substituted alkyl halide in the presence of potassium carbonate to yield thiyridnes of the formula K-2.

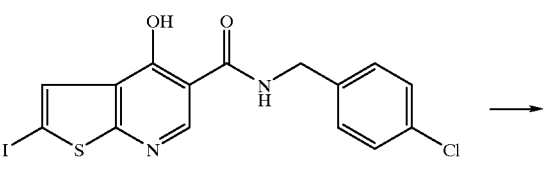

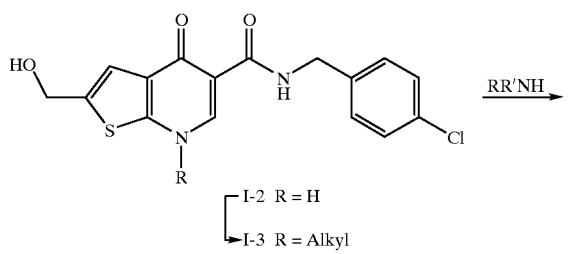

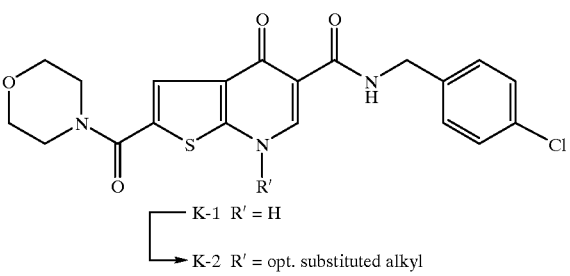

Chart J.

N-(4-Chlorobenzyl)-4-hydroxythieno[2,3-b]pyridine-5-carboxamide (A-6 where R=H) undergoes a Mannich reaction by heating with morpholine and formaldehyde in acetic acid/ethanol to afford 2-morpholinomethyl derivative J-1. Compound J-1 is then treated with an optionally substituted alkyl halide in the presence of potassium carbonate or with an optionally substituted alcohol under Mitsunobu conditions to yield thienopyridones of the general formula J-2.

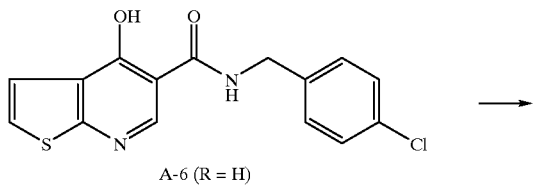

Chart L.

Aminomethylenemalonate L-2 is prepared as described in German patent 2447477 (1976) from tert-butyl 2-aminothiophene-3-carboxylate (L-1) (M. Gutschow and U. Neumann, J. Med. Chem. 1998, 41, 1729–1740) by reacting with diethyl ethoxymethylenemalonate. Intermediate L-2 is then alkylated at nitrogen by reaction with iodomethane in the presence of potassium carbonate affording L-3. Subsequently, L-3 undergoes a Mannich reaction with 4-methylene morpholinium chloride (Dimmock, JR, et al. Eur. J. Med. Chem. 1989, 24, 379–383) to provide the morpholinomethyl intermediate L4. Thieno[2,3-b]pyridone L-5 is then prepared by heating compound L4 in a mixture of Eaton's reagent. Ester L-5 is then treated with a benzylamine (e.g. 4-chlorobenzylamine, 4-bromobenzylamine, or 4-fluorobenzylamine) at high temperature to afford the corresponding amides of the general formula L-7 or ester L-5 may be saponified to afford acid L-6 which is then coupled with a benzylamine to provide amides of the general formula L-7.

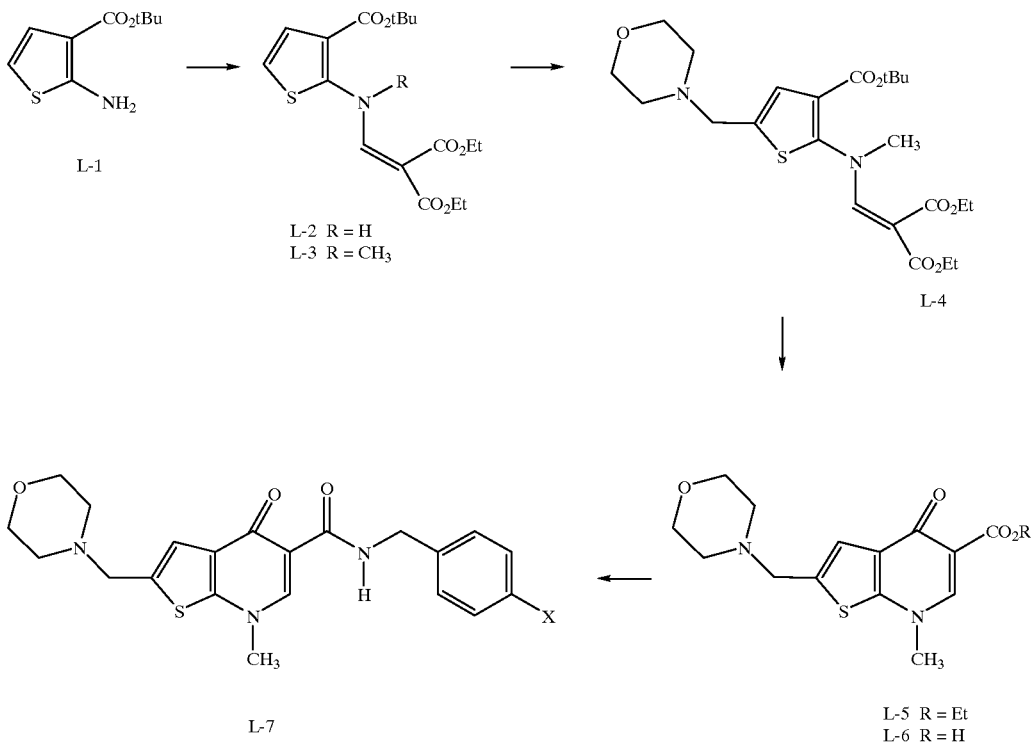

L-1

L-2 R = H
L-3 R = CH₃

L-4

L-7

L-5 R = Et
L-6 R = H

Chart M

Compounds of the invention wherein $R^2$ is (a) $R^5$; (b) $NR^7R^8$; or (c) $OR^9$ and $R^5$ is (a) het, wherein said het is bound via carbon; (b) aryl; (c) $C_{3-8}$cycloalkyl which may be partially unsaturated and optionally substituted by one or more substituents selected from a group consisting of $R^{11}$, $NR^7R^8$, $SO_mR^9$, and $C_{1-7}$alkyl optionally substituted by $R^{11}$, $NR^7R^8$, or $SO_mR^9$; or (d) tert-butyl, are prepared as exemplified in Chart M. Intermediates bearing the 4-oxo4,7-dihydrothieno[2,3-b]pyridine ring system are prepared in a manner analogous to that precedent in the literature (M. M. El-Abedelah, M. Z. Nazer, S. F. Okasha, M. Calas, J. Bompart, P. Mion Eur. J. Med. Chem. 1998, 33, 33–42; and M. M. El-Abedelah, S. S. Sabri, A. A. Al-Ashqar Hetrocycles 1997, 45, 255–264). 2-Bromo-5-chloro-4-thiophenecarboxylic acid (M-1) (prepared as described by S. Ol, H. Nagaya, N. Inatomi, M. Nakao, H. Yukimasa WO-97/11705, 1997) is activated with 1,1'-carbonyldiimidazole and is then treated with ethyl trimethylsilyl malonate in the presence of DBU to afford 3-ketoester M-2. Refluxing compound M-2 in acetic anhydride and triethylorthoformate provides enol ether M-3. Compound M-3 is then contacted with a nitrogen containing compound of the formula $RNH_2$ where R may be, but is not limited to, the $R^2$ definition above (e.g., cyclopropylamine, tert-butylamine, aniline, 3-furylamine, 4-aminomorpholine, 1-amino-4-methylpiperazine, or O-ethylhydroxylamine) to afford a compound of formula M-4. The reaction can conveniently be carried out in ethanol. The resulting enamines M-4 are then cyclized by heating with sodium hydride (or other appropriate base) in tetrahydrofuran to afford the thieno[2,3-b]pyridine-5-carboxylic esters of formula M-5. The esters M-5 are heated in the presence of a substituted benzylamine (e.g., 4-chlorobenzylamine) and iodine to afford the corresponding carboxamides of the formula M-6. Alternatively, carboxamides of formula M-6 are prepared such that the esters M-5 are saponified in the presence of aqueous sodium hydroxide affording the corresponding carboxylic acid which is then coupled with a substituted benzylamine in the presence of 1,1'-carbonyldiimidazole. Compounds of the formula M-6 are transformed to derivatives in analogous fashion to that described in charts G and K. Specifically, compounds of formula M-6 are coupled with propargylic alcohol in the presence of $Pd(PPh_3)_2Cl_2$, CuI, and diethylamine to afford compounds of the formula M-7. Saturation of the alkynyl functionality present in M-7 by hydrogenation over a palladium catalyst provides compounds of the formula M-8.

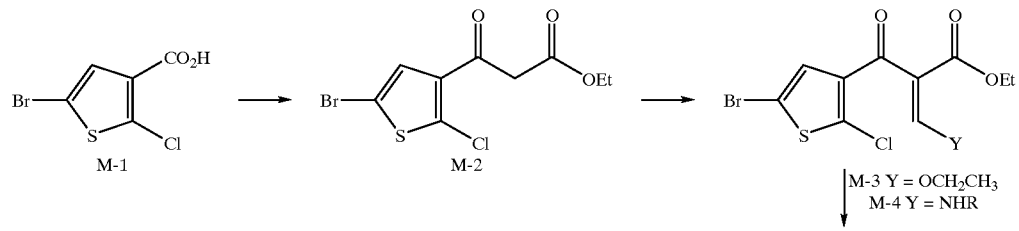

M-1

M-2

M-3 Y = OCH₂CH₃
M-4 Y = NHR

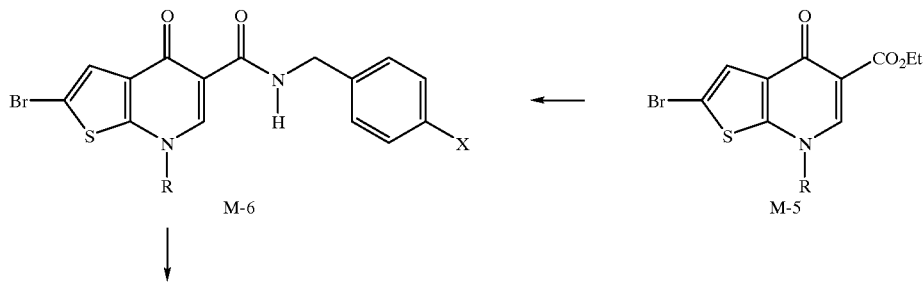

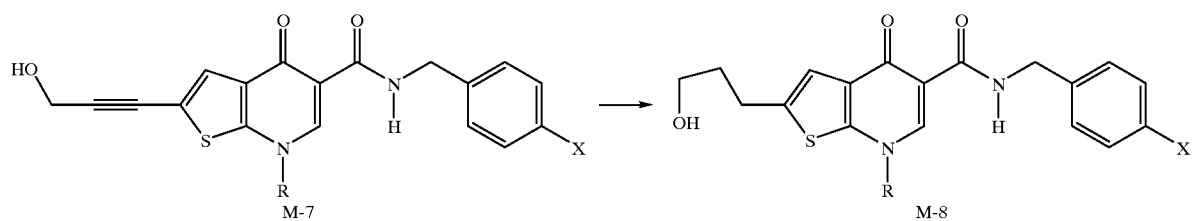

Chart N

Alternatively, a subset of compounds bearing the $R^2$ definition in Chart M where $R^3$ is $CH_2NR^7R^8$ are prepared as exemplified in Chart N. 3-Bromo-2-chlorothiophene (N-1) (prepared as described by J. J. Baldwin, J. M. Hoffman, J. H. Jones, C. S. Rooney, A. M. Smith U.S. Pat. No. 5,276,025; 1994) is metalated with lithium diisopropylamide in tetrahydrofuiran followed by quenching with N,N-dimethylformamide to afford carboxaldehyde N-2. Reductive amination of N-2 by treating with an amine (e.g., morpholine), acetic acid, and sodium triacetoxyborohydride affords thiophene N-3. Metalation of the compound N-3 with n-BuLi followed by trapping with carbon dioxide provides carboxylic acid N-4. Acid N-4 is activated with 1,1'-carbonyldiimidazole and is then treated with ethyl trimethylsilyl malonate in the presence of DBU to afford 3-ketoester N-5. Refluxing compound N-5 in acetic anhydride and triethylorthoformnate provides enol ether N-6.

Compound N-6 is then contacted with a nitrogen containing compound of the formula $RNH_2$ where R may be but is not limited to the $R^2$ definition above (e.g., cyclopropylamine, tert-butylamine, aniline, 3-furylamine, 4-aminomorpholine, 1-amino4-methylpiperazine, or O-ethylhydroxylamine) to afford a compound of formula N-7. The reaction can conveniently be carried out in ethanol, The resulting enamines N-7 are then cyclized by heating with sodium hydride (or other appropriate base) in tetrahydrofuran to afford the thieno[2,3-b]pyridine-5-carboxylic esters of formula N-8. The esters N-8 are heated in the presence of a substituted benzylamine (e.g., 4-chlorobenzylamine) to afford the corresponding carboxamides of the formula N-9. Alternatively, carboxamides of formula N-9 are prepared such that the esters N-8 are saponified in the presence of aqueous sodium hydroxide in affording the corresponding carboxylic acid which is then coupled with a substituted benzylamine in the presence of 1,1'-carbonyldiimidazole.

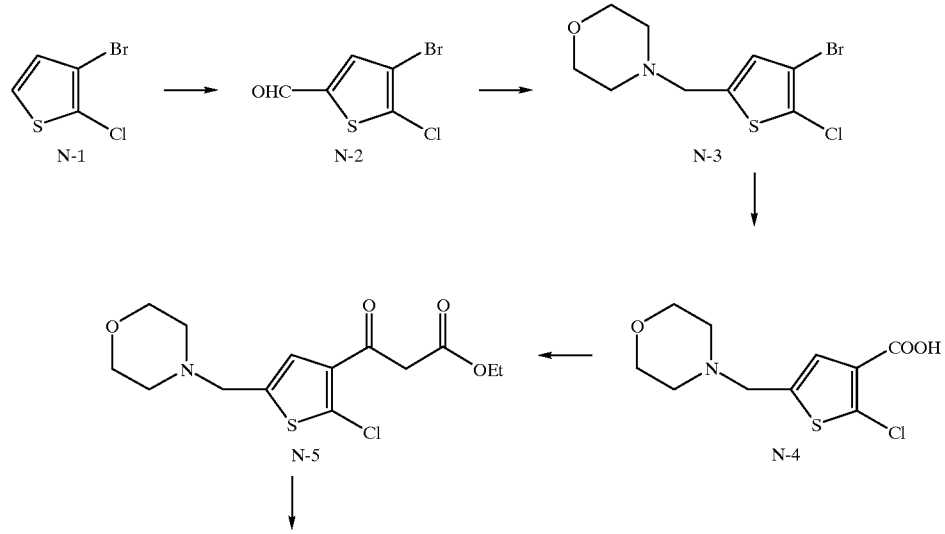

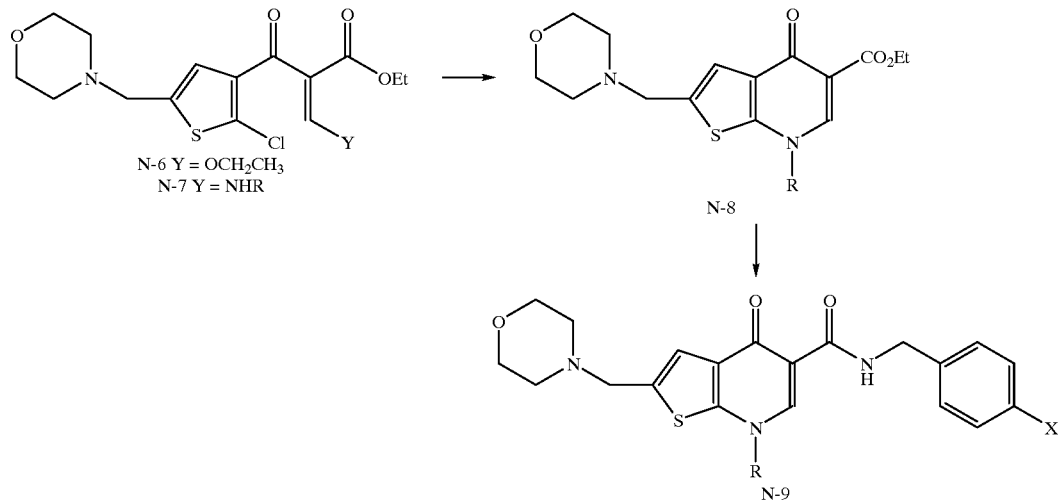

N-6 Y = OCH₂CH₃
N-7 Y = NHR

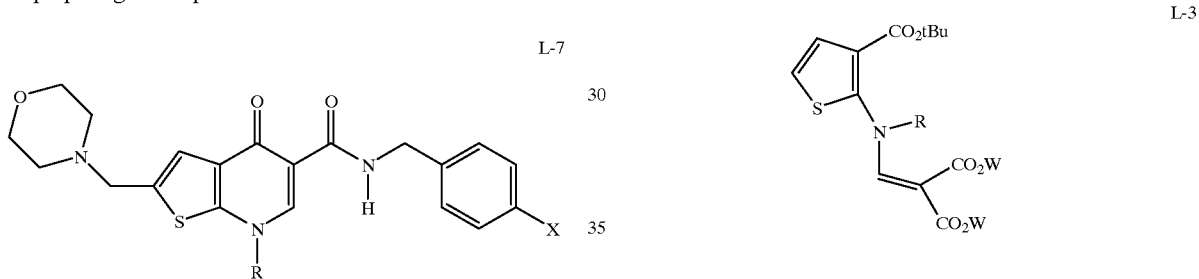

N-8

N-9

The invention also provides processes and intermediates described herein that are useful for preparing compounds of the invention. For example, the invention provides a method for preparing a compound of formula L-7:

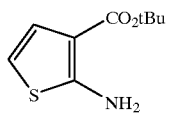

L-7 wherein R is $C_{1-4}$alkyl; and X is Cl, Br, CN, $NO_2$, or F, comprising steps 1–6 described below.

(1) Reacting an amine of formula L-1:

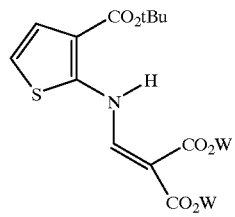

L-1 with an alkoxymethylenemalonate of formula R'OCH=CH($CO_2W$)₂ wherein R' is $C_{1-4}$alkyl and each W is independently selected from $C_{1-4}$alkyl, to provide a compound of formula L-2:

L-2

The reaction can conveniently be carried out by heating a solution of compound L-1 with the alkoxymethylenemalonate, or an equivalent thereof.

(2) Alkylating the compound of formula L-2 to provide a corresponding compound of formula L-3:

L-3

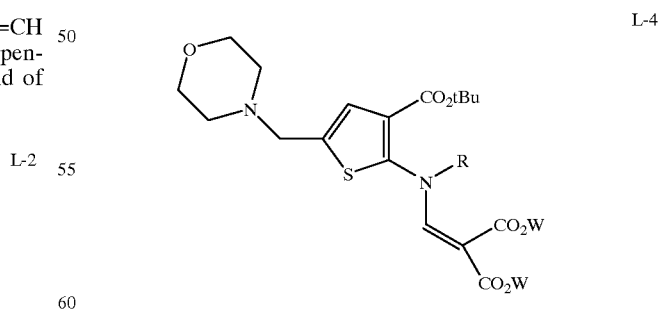

wherein R is $C_{1-4}$alkyl. The reaction can conveniently be carried out by contacting the compound of formula L-2 with an iodoalkane of formula I-R in the presence of a suitable base (e.g. an alkali metal carbonate).

(3) Reacting the compound of formula L-3 with a 4-methylenemorpholinium salt to provide a compound of formula L-4:

L-4

The reaction can conveniently be carried out by contacting the ester with a suitable 4-methylenemorpholinium salt or with a combination of reagents that generates a 4-methylenemorpholinium salt in situ.

(4) Cyclizing the compound of formula L-4 under conditions suitable to provide a bicyclic ester of formula L-5:

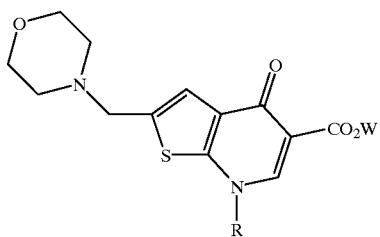

L-5

The cyclization can conveniently be carried out by contacting a compound of formula L-4 with a mixture of phosphorus pentoxide and methanesulfonic acid.

(5) Hydrolyzing the ester L-5 to provide a carboxylic acid of formula L-6:

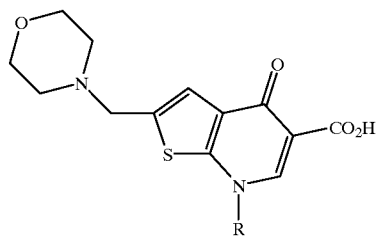

L-6

Suitable conditions for converting an ester to a corresponding carboxylic acid are well known in the art. The reaction can be carried out under any suitable conditions.

(6) Reacting the carboxylic acid formula L-6 with a 4-substituted benzyl amine to provide the compound of formula L-7. Suitable conditions for preparing an amide from a corresponding carboxylic acid are well known in the art. The reaction can be carried out under any suitable conditions. For example, the reaction can conveniently be carried out by activating the carboxylic acid with a suitable activating agent, and treating the resulting activated acid with the requisite 4-substituted benzyl amine to provide the compound of formula L-7.

The invention also provides a method for preparing a compound of formula (I) wherein $R^1$–$R^4$ have any of the values, specific values, or preferred values described herein, comprising reacting a corresponding carboxylic acid of formula (II):

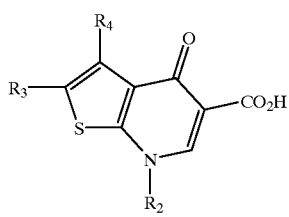

(II)

with a benzyl amine of the formula:

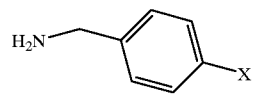

wherein X is Cl, Br, CN, $NO_2$, or F, under conditions suitable to provide the compound of formula (I). Suitable conditions for preparing an amide from a corresponding carboxylic acid are well known in the art. The reaction can be carried out under any suitable conditions. For example, the reaction can conveniently be carried out by activating the carboxylic acid with a suitable activating agent, and treating the activated acid with the requisite 4-substituted benzyl amine to provide the compound of formula (I). Suitable amines include 4-chlorobenzylamine, 4-fluorobenzylamine, 4-bromobenzylamine, 4-cyanobenzylamine, and 4-nitrobenzylamine.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478),. Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A.

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPE (pH 7.5), 11.7 mM KCl, 4.5 mM $MgCl_2$, 0.36 mg/ml BSA, and 90 nM $^3$H-dTTP. Assays are run with and without CHAPS, (3-[(3-cholamidopropyl)-dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/ml BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly(dA)-oligo(dT) template/primer to reaction mixtures containing the enzyme, substrate, and compounds of interest. Plates are incubated in a 25 C or 37 C $H_2O$ bath and terminated via the addition of 40 μl/reaction of 0.5 M EDTA (pH 8) per well. Reactions are terminated within the timeframe during which substrate incorporation is linear and varied depending upon the enzyme and conditions used, i.e., 30 min. for HCMV polymerase. Ten μl of streptavidin-SPA beads (20 mg/ml in PBS/10% glycerol) are added following termination of the reaction. Plates are incubated 10 min. at 37 ° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiothreotol (DTT) is added to the polymerase buffer. Also, a different lot of CMV polymerase is used, which appears to be more active resulting in a more rapid polymerase reaction. Results of the testing of representative compounds of formula I in this assay are shown in Table 1. In Table 1, the term "nd" refers to activity data not determined.

TABLE 1

Biological Data

| | polymerase $IC_{50}$ (μM) | | |
|---|---|---|---|
| Example | HCMV | HSV | VZV |
| 1 | 28.9 | nd | nd |
| 2 | 6.3 | nd | nd |
| 3 | 15.9 | nd | nd |
| 4 | 10.8 | nd | nd |
| 5 | 2.5 | 0.88 | 0.60 |
| 6 | 5.8 | nd | nd |
| 7 | 8.0 | nd | nd |
| 8 | 2.2 | 0.91 | 0.55 |
| 9 | 12.5 | nd | nd |
| 10 | 34.3 | nd | nd |
| 11 | 18.8 | nd | nd |
| 12 | 11.0 | nd | nd |
| 13 | 9.0 | nd | nd |
| 14 | 1.8 | nd | nd |
| 15 | 4.7 | 3.2 | 1.9 |
| 16 | 0.67 | nd | nd |
| 17 | 0.92 | 0.89 | 0.28 |
| 18 | 1.7 | 0.95 | 0.39 |
| 19 | 0.86 | nd | nd |
| 20 | 0.18 | nd | nd |
| 21 | <0.78 | nd | nd |
| 22 | 0.81 | nd | nd |
| 23 | 2.9 | nd | nd |
| 24 | 1.0 | nd | nd |
| 25 | 0.4 | 0.45 | 0.46 |
| 26 | 14.2 | nd | nd |
| 27 | 4.2 | nd | nd |
| 28 | 2.4 | nd | nd |
| 29 | 6.5 | nd | nd |
| 30 | 28.2 | nd | nd |
| 31 | 15.4 | nd | nd |
| 32 | >50.0 | nd | nd |
| 33 | 22.4 | nd | nd |
| 34 | >20.0 | nd | nd |
| 35 | 18.5 | nd | nd |
| 36 | 1.8 | 1.2 | 0.77 |
| 37 | nd | nd | nd |
| 38 | 2.6 | nd | nd |
| 39 | <0.31 | nd | nd |
| 40 | <0.31 | nd | nd |
| 41 | 3.4 | nd | nd |
| 42 | 1.9 | nd | nd |
| 43 | 1.9 | nd | nd |
| 44 | 4.7 | nd | nd |
| 45 | 2.6 | nd | nd |
| 46 | 3.8 | nd | nd |
| 47 | >20.0 | nd | nd |
| 48 | 19.0 | nd | nd |
| 49 | 3.2 | nd | nd |
| 50 | 3.8 | nd | nd |
| 51 | 1.2 | nd | nd |
| 52 | 1.5 | nd | nd |
| 53 | 4.0 | nd | nd |
| 54 | 3.2 | nd | nd |
| 55 | 5.0 | nd | nd | nd = not determined.

DESCRIPTION OF PREFERRED EMBODIMENTS

EXAMPLE 1

N-(4-Chlorobenzyl)-4-hydroxythieno[2,3-b]pyridine-5-carboxamide

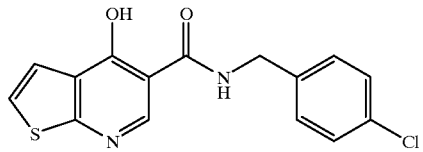

A mixture of ethyl 4-hydroxythieno[2,3-b]pyridine-5-carboxylate (J. Heterocyclic Chem. 1977, 14, 807) (0.447 g) and 4-chlorobenzylamine (2.43 mL) is stirred at 190° C. for 1 h. The reaction is then allowed to cool to rt and is diluted with toluene (5 mL). The resulting precipitate is filtered off and washed with toluene followed by hexanes to yield an off-white solid. This material is recrystallized from acetic acid/water then ethanol to yield 0.285 g (45%) of the title compound as a white solid.

Physical characteristics are as follows:

Mp 238–240° C.; $^1$H NMR (300 MHz, DMSO-$d_6$) δ 813.37, 10.56, 8.71, 7.43–7.34, 4.54; $^{13}$C NMR (75 MHz, TFA) δ 169.0, 167.1, 153.6, 139.5, 134.7, 133.2, 128.8, 128.8, 127.8, 127.6, 107.9, 43.8; IR (mull) 2785, 2753, 2694, 2672, 2317, 1996, 1668, 1541, 1498, 1432, 1398, 1348, 803, 700, 610 cm$^{-1}$; MS(ESI−) m/z 317 (M−H)$^-$; Anal. Found: C, 56.30; H, 3.61; N, 8.72; Cl, 11.08; S, 9.98.

EXAMPLE 2

N-(4-Chlorobenzyl)-4-hydroxy-2-iodothieno[2,3-b]pyridine-5-carboxamide

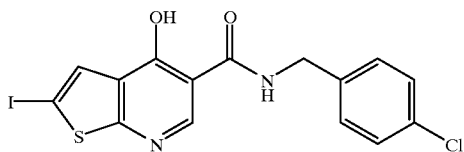

Mercuric oxide (7.10 g) and iodine (8.32 g) are added portion-wise to a solution of ethyl 4-hydroxythieno[2,3-b]pyridine-5-carboxylate (J. Heterocyclic Chem. 1977, 14, 807) (5.22 g) in CHCl$_3$ (90 mL). The reaction is stirred at rt for 18 h. The reaction mixture is filtered, and the solid is washed with CHCl$_3$ (400 mL). The organic layer is washed with H$_2$O (200 mL), dried with MgSO$_4$, filtered, and concentrated in vacuo. The resulting orange solid is purified by column chromatography (CH$_2$Cl$_2$:heptane, 1:1). Fractions homogeneous by TLC are combined and concentrated in vacuo to yield 2.95 g (36%) of ethyl 4-hydroxy-2-iodothieno[2,3-b]pyridine-5-carboxylate as a pale yellow solid. Ethyl 4-hydroxy-2-iodothieno[2,3-b]pyridine-5-carboxylate (2.64 g) is suspended in 10% NaOH (21 mL) and heated to reflux. The reaction is stirred at reflux for 1 h and then cooled to rt. The reaction mixture is poured into H$_2$O (80 mL). Conc. HCl is added until a precipitate forms, and 2.272 g (94%) of 4-hydroxy-2-iodothieno[2,3-b]pyridine-5-carboxylic acid is isolated as a white solid. Carbonyldiimidazole (1.34 g) is added to a solution of 4-hydroxy-2-iodothieno[2,3-b]pyridine-5-carboxylic acid (2.041 g) in DMF (58 mL). The reaction is heated to 60° C. and stirred for 18 h. The reaction mixture is cooled to rt, and 4-chlorobenzylamine (1.01 mL, 8.27) is added. The reaction is stirred at rt for 7 h. The reaction mixture is poured into 20% aqueous HOAc (180 mL), and the resulting white solid is filtered off. This material is recrystallized from methanol then toluene to yield 2.095 g (74%) of the title compound as a white solid.

Physical characteristics are as follows:

Mp 231–232 (dec) ° C.; $^1$H NMR (300 MHz, DMSO-$d_6$) δ 13.27, 10.43, 8.69, 7.63, 7.41–7.33, 4.53; $^{13}$C NMR (75 MHz, DMSO-$d_6$) δ 165.0, 142.1, 139.0, 133.1, 131.9, 131.2, 129.6, 128.8, 113.9, 74.5, 41.9; IR (drift) 3172, 3060, 2993, 2923, 2908, 2841, 1639, 1588, 1537, 1509, 1497, 1473, 1293, 802, 785, cm$^{-1}$; MS (ESI−) for m/z 443 (M−H)$^-$; Anal. Found: C, 40.75; H, 2.41; N, 6.44; Cl, 7.81; S, 7.01.

EXAMPLE 3

N-(4-Chlorobenzyl)-4-hydroxy-2-(4-morpholinylsulfonyl)-thieno[2,3-b]pyridine-5-carboxamide

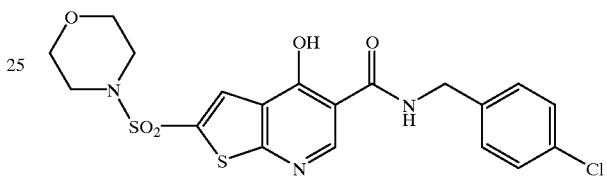

Morpholine (1.69 mL) is dissolved in CH$_2$Cl$_2$ (40 mL). Triethylamine (6.8 mL) is added, and the reaction is cooled to 0° C. A solution of 5-nitro-2-thiophenesulfonyl chloride (3.69 g) in CH$_2$Cl$_2$ (25 mL) is then added dropwise. The reaction is stirred at 0° C. for 15 min. and then at room temperature for 30 min. The reaction mixture is concentrated in vacuo, and the resulting brown solid is purified via column chromatography (CH$_2$Cl$_2$). Fractions homogeneous by TLC are combined and concentrated in vacuo to yield 3.52 g (78%) of 2-morpholinosulfonyl-5-nitrothiophene as a yellow solid. 2-morpholinosulfonyl-5-nitrothiophene (3.40 g) and conc. HCl (27 mL) are combined and heated to 40° C. SnCl$_2$.2H$_2$O (7.72 g) is added portion-wise while keeping the reaction temperature between 40–45° C. using an ice bath. After the addition is complete, the reaction is stirred at 40° C. for 1 h. The reaction mixture is cooled to room temperature, diluted with H$_2$O (100 mL), and the solution is adjusted to pH 11 with NH$_4$OH. The aqueous layer is extracted with ethyl acetate (3×250 mL). The combined organic layers are dried with MgSO$_4$, filtered, and concentrated in vacuo to yield 2.83 g of 2-amino-5-morpholinosulfonylthiophene as a brown solid. 2-amino-5-morpholinosulfonylthiophene (2.12 g) and diethylethoxymethylene majonate (1.73 mL) are combined and heated to 135° C. The reaction is stirred at 135° C. for 1 h. The reaction is then cooled for several minutes and is diluted with heptane. The product oils out, so the mixture is concentrated in vacuo and the residue is purified via column chromatography (CH$_2$Cl$_2$:CH$_3$OH, 98:2). Fractions homogeneous by TLC are combined and concentrated in vacuo to yield 1.89 g (53%) of the intermediate malonate as a brown oil. This material is combined with diphenyl ether (5 mL). The reaction mixture is degassed and then heated to reflux. The reaction is stirred at reflux for 1 h. The reaction mixture is allowed to cool for several minutes and is diluted with heptane. The resulting tan solid is filtered off and purified via column chromatography (CH$_2$Cl$_2$, CH$_2$Cl$_2$:CH$_3$OH, 98:2). Fractions homogeneous by TLC are combined and concentrated in vacuo to yield 0.537 g (43%) of 4-hydroxy-2-morpholinosulfonyl-thieno[2,3-b]pyridine-5-carboxylic acid, ethyl ester as a light brown solid. A mixture of 4-hydroxy-2-morpholinosulfonyl-thieno[2,3-b]pyridine-5-carboxylic acid, ethyl ester (0.503 g) and 4-chlorobenzylamine (1.64 mL) is stirred at 190° C. for 1 h. The reaction is then allowed to cool to rt and is diluted with toluene. The resulting precipitate is filtered off and washed with toluene followed by hexanes to yield a tan solid. This material is recrystallized from acetic acid/water then ethanol to yield 0.240 g (38%) of the title compound as a tan solid.

Physical characteristics are as follows:

Mp>300° C.; $^1$H NMR (300 MHz, DMSO-d$_6$) δ 13.45, 10.29, 8.86, 7.81, 7.42–7.33, 4.55, 3.68, 3.02; $^{13}$C NMR (75 MHz, DMSO-d$_6$) δ 173.7, 164.5, 151.8, 144.3, 138.9, 131.9, 130.8, 129.6, 129.1, 128.8, 128.1, 114.7, 65.7, 46.3, 41.9; IR (mull) 3156, 1648, 1598, 1536, 1500, 1491, 1352, 1340, 1334, 1260, 1155, 1115, 1076, 945, 733 cm$^{-1}$; MS (FAB) m/z 468 (MH$^+$); HRMS (FAB) found 468.0458; Anal. Found: C, 48.69; H, 4.10; N, 8.91; Cl, 7.51; S, 13.76.

EXAMPLE 4

2-Bromo-N-(4-chlorobenzyl)-4-hydroxythieno[2,3-b]pyridine-5-carboxamide

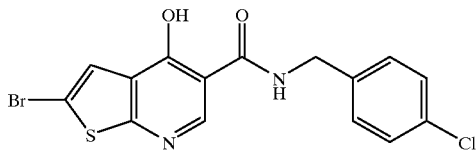

To a solution of ethyl 4-hydroxythieno[2,3-b]pyridine-5-carboxylate (J. Heterocyclic Chem. 1977, 14, 807) (1.00 g) in CHCl$_3$ (26 mL) is added bromine (0.23 mL) dropwise. The reaction is stirred at rt for 2 h. The reaction mixture is poured into 2N HCl (30 mL), and the aqueous layer is extracted with CHCl$_3$ (3×30 mL). The combined organic layers are washed with H$_2$O (100.mL), dried with MgSO$_4$, filtered and concentrated in vacuo to yield 0.840 g (62%) of the bromide as a yellow solid. This material (0.757 g) is suspended in 10% aqueous NaOH (7 mL) and heated to reflux. The reaction is stirred at reflux for 1 h. The reaction mixture is cooled to rt, and H$_2$O (26 mL) is added. Conc. HCl is added until a precipitate forms. The precipitate is filtered off to yield 0.597 (87%) of the acid as a brown solid. Carbonyldiimidazole (0.530 g) is added to a solution of 2-bromo-4-hydroxy-thieno-[2,3-b]pyridine-5-carboxylic acid (0.597 g) in DMF (20 mL). The reaction is heated to 60° C. and stirred for 18 h. The reaction mixture is cooled to rt, and 4-chlorobenzylamine (1.01 mL) is added. The reaction is stirred at rt for 7 h. The reaction mixture is poured into 20% aqueous HOAc (180 mL), and the resulting white solid is filtered off. This material is recrystallized from methanol then toluene to yield 2.095 g (74%) of the title compound as a white solid.

Physical characteristics are as follows:

Mp 234–236° C.; $^1$H NMR (300 MHz, DMSO-d$_6$) δ 13.25, 10.41, 8.74, 7.52, 7.41–7.33, 4.53; $^{13}$C NMR (75 MHz, TFA) δ 167.7, 166.9, 153.9, 139.1, 134.7, 133.2, 129.0, 128.9, 128.1, 122.3, 116.7, 108.6, 43.8; IR (drift) 3187, 3098, 3074, 3024, 2927, 2842, 1645, 1592, 1541, 1503, 1338, 1287, 916, 792, 689 cm$^-$; MS (ESI-) m/z 397 (M−H)$^-$; Anal. Found: C, 45.03; H, 2.73; N, 6.98; Br, 19.72; Cl, 8.70; S, 7.96.

EXAMPLE 5

N-(4-Chlorobenzyl)-4-hydroxy-2-(3-hydroxy-1-propynyl)thieno[2,3-b]pyridine-5-carboxamide

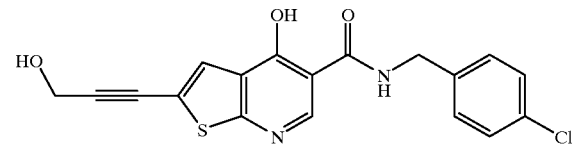

To a suspension of N-(4-chlorobenzyl)-4-hydroxy-2-iodothieno[2,3-b]pyridine-5-carboxamide (Example No. 2) (1.00 g) in diethylamine (28 mL) is added copper iodide (0.128 g) and Pd(PPh$_3$)$_2$Cl$_2$ (0.032 g) followed by addition of propargyl alcohol (0.16 mL). The reaction is stirred at rt for 3 d. The reaction mixture is partitioned between H$_2$O (100 mL) and ethyl acetate (100 mL). The organic layer is removed, and the aqueous layer is extracted with ethyl acetate (2×100 mL). Combined organic layers are washed with a saturated aqueous NH$_4$Cl solution, dried with MgSO$_4$, filtered, and concentrated in vacuo. The resulting orange solid is purified via column chromatography (CH$_2$Cl$_2$:CH$_3$OH; 98:2, 95:5). Fractions homogeneous by TLC are combined and concentrated in vacuo to yield a pale orange solid which is recrystallized from CH$_2$Cl$_2$/CH$_3$OH to yield 0.165 g (20%) of the title compound as an off-white solid.

Physical characteristics are as follows:

Mp 233–236° C.; $^1$H NMR (300 MHz, DMSO-d$_6$) δ 13.32, 10.41, 8.75, 7.49, 7.41–7.33, 5.44, 4.53, 4.34; $^{13}$C NMR (75 MHz, DMSO-d$_6$) δ 172.8, 164.9, 148.8, 143.0, 131.9, 130.9, 129.6, 128.8, 126.8, 117.1, 114.2, 96.4, 76.6, 50.0, 41.9; IR (drift) 3239, 3107, 2944, 2888, 2872, 2239, 1650, 1581, 1550, 1513, 1345, 1312, 1041, 819, 790 cm$^{-1}$; MS (ESI-) for m/z 371 (M−H)$^-$; Anal. Found: C, 57.87; H, 3.58; N, 7.59; Cl, 9.38; S, 8.48.

EXAMPLE 6

N-(4-Chlorobenzyl)-4-hydroxy-2-(3-methoxy-1-propynyl)-thieno[2,3-b]pyridine-5-carboxamide

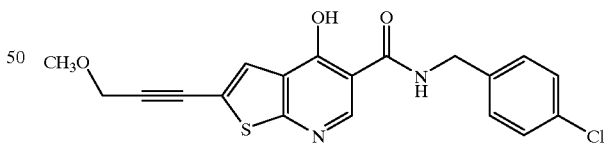

To a suspension of N-(4-chlorobenzyl)4-hydroxy-2-iodothieno[2,3-b]pyridine-5-carboxamide (Example No. 2) (1.00 g) in diethylamine (28 mL) is added copper iodide (0.128 g), and Pd(PPh$_3$)$_2$Cl$_2$ (0.079 g) followed by addition of propargyl methyl ether (0.27 mL). The reaction is stirred at rt for 18 h. The reaction mixture is partitioned between H$_2$O (100 mL) and CH$_2$Cl$_2$ (100 mL). The organic layer is removed, and the aqueous layer is extracted with CH$_2$Cl$_2$ (3×100 mL). Combined organic layers are washed with a saturated aqueous NH$_4$Cl solution (200 mL), dried with MgSO$_4$, filtered, and concentrated in vacuo. The resulting brown oil is purified via column chromatography (CH₂Cl₂:CH₃OH; 98:2). The resulting impure material is re-purified via column chromatography (heptane:2-propanol, 10:1; CH₂Cl₂:CH₃OH, 98:2). Fractions homogeneous by TLC are combined and concentrated in vacuo to yield to yield 0.260 g (30%) of the title compound as an off-white solid.

Physical characteristics are as follows:

Mp 215–218° C.; ¹H NMR (300MHz, DMSO-d₆) δ 13.33, 10.40, 8.76, 7.56, 7.41–7.33, 4.55, 3.33; ³C NMR (75 MHz, DMSO-d₆) δ 164.8, 143.1, 139.0, 131.9, 129.6, 128.8, 127.6, 116.4, 114.2, 92.5, 78.7, 60.0, 57.7, 41.9; IR (drift) 3176, 3074, 3016, 2924, 2859, 2822, 2320, 2218, 1640, 1587, 1534, 1512, 1353, 1097, 783 cm⁻¹; MS (ESI-) for m/z 385 (M-H)⁻; Anal. Found: C, 58.84; H, 4.09; N, 7.28; Cl, 9.16; S, 8.32.

EXAMPLE 7

N-(4-Chlorobenzyl)-4-hydroxy-2-(4-hydroxy-1-butynyl)thieno[2,3-b]pyridine-5-carboxamide

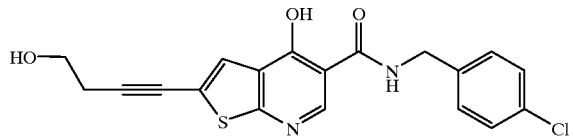

To a suspension of N-(4-chlorobenzyl)-4-hydroxy-2-iodothieno[2,3-b]pyridine-5-carboxamide (Example No. 2) (1.00 g) in diethylamine (28 mL) is added copper iodide (0.128 g) and Pd(PPh₃)₂Cl₂ (0.032 g) followed by addition of 3-butyn-1-ol (0.20 mL). The reaction is stirred at rt for 18 h. The reaction mixture is partitioned between H₂O (100 mL) and ethyl acetate (100 mL). The organic layer is removed, and the aqueous layer is extracted with ethyl acetate (2×100 mL). Combined organic layers are dried with MgSO₄, filtered, and concentrated in vacuo. The resulting brown oil is purified via column chromatography (CH₂Cl₂:CH₃OH; 98:2). Fractions homogeneous by TLC are combined and concentrated in vacuo to yield a brown solid. This material is dissolved in DMF (15 mL) and 2N HCl is added until a precipitate forms. The resulting tan solid is purified via column chromatography (CH₂Cl₂:CH₃OH; 98:2, 95:5). Fractions homogeneous by TLC are combined and concentrated in vacuo to yield 0.183 g (21 %) of the title compound as a yellow, crystalline solid.

Physical characteristics are as follows:

Mp 242–246° C.; ¹H NMR (300 MHz, DMSO-d₆) δ 13.31, 10.43, 8.73, 7.41–7.33, 4.95, 4.54, 3.59, 2.62; IR (drift) 2934, 2915, 2845, 2771, 2352, 2327, 2224, 1965, 1920, 1662, 1646, 1587, 1538, 1515, 1500 cm⁻¹; MS (ESI-) for m/z 385 (M-H)⁻. Anal. Found: C, 58.61; H14.05; N, 7.18; Cl, 9.02; S, 8.11.

EXAMPLE 8

N-(4-Chlorobenzyl)4-hydroxy-2-(3-hydroxpropyl)thieno[2,3-b]pyridine-5-carboxamide

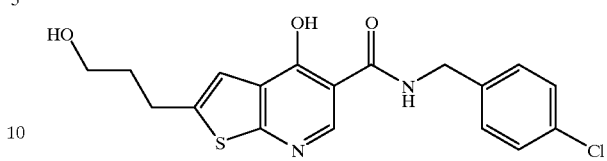

A solution of N-(4-chlorobenzyl)4-hydroxy-2-(3-hydroxy-1-propynyl)-thieno[2,3-b]pyridine-5-carboxamide (Example No. 5) (0.300 g) in 1/1 CH₂Cl₂/CH₃OH (70 mL) is hydrogenated over 10% Pd/C (90 mg) at 35 psi. After 3 h, an additional 90 mg of 10% Pd/C is added, and the solution is hydrogenated at 35 psi for 1 h. The reaction mixture is filtered through a Celite pad, and the filtrate is concentrated in vacuo. The resulting pale orange solid is purified via column chromatography (CH₂Cl₂:CH₃OH; 98:2, 95:5). Fractions homogeneous by TLC are combined and concentrated in vacuo to yield and off-white solid which is recrystallized from ethanol to yield 0.083 g (27%) of the title compound as a white, crystalline solid.

Physical characteristics are as follows:

Mp 185–186° C.; ¹H NMR (300 MHz, DMSO-d₆) δ 13.29, 10.61, 8.64, 7.42–7.33, 7.11, 4.54, 3.45, 2.87, 1.80; ¹³C NMR (75 MHz, DMSO-d₆) 173.1, 165.2, 147.3, 141.3, 140.5, 139.1, 131.9, 129.6, 128.8, 118.7, 113.8, 60.0, 41.9, 34.3, 26.5; IR (drift) 3224, 2929, 2886, 2846, 2817, 2750, 2327, 1906, 1657, 1604, 1541, 1489, 1470, 802, 698 cm⁻¹; MS (ESI-) for m/z 376 (M-H)⁻; Anal. Found: C, 57.06; H, 4.50; N, 7.40; Cl, 9.25; S, 8.35.

EXAMPLE 9

N-(4-Chlorobenzyl)-2-cyano-4-hydroxythieno[2,3-b]pyridine-5-carboxamide

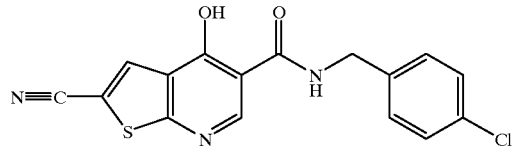

To a solution of N-(4-chlorobenzyl)4-hydroxy-2-iodothieno[2,3-b]pyridine-5-carboxamide (Example No. 2) (0.500 g) in pyridine (5 mL) is added CuCN (0.201 g). The reaction is heated to reflux and stirred for 18 h. The reaction mixture is purified via column chromatography (CH₂Cl₂:CH₃OH; 98:2). Fractions homogeneous by TLC are combined and concentrated in vacuo to yield a pale yellow solid which is recrystallized from methanol to yield 0.100 g (26%) of the title compound as an off-white solid.

Physical characteristics are as follows:

Mp 274–276° C. (dec); ¹H NMR (300 MHz, DMSO-d₆) δ 13.30, 10.24, 8.68, 8.28, 7.41–7.33, 4.54; ¹³C NMR (75 MHz, DMSO-d₆) δ 173.1, 164.5, 152.1, 144.4, 138.8, 135.2, 131.9, 129.6, 128.8, 114.5, 103.4, 42.0; IR (drift) 3306, 3097, 3003, 2921, 2844, 2220, 1638, 1587, 1524, 1484, 1398, 1342, 1298, 884, 791 cm⁻¹; HRMS (El) found 343.1082; Anal. Found: C, 55.31; H, 2.88; N, 12.02; Cl, 9.95; S, 9.04.

EXAMPLE 10

Dimethyl 2-[3-(5-{[(4-Chlorobenzyl)amino]carbonyl}-4-hydroxythieno[2,3-b]pyridin-2-yl)-2-propynyl]malonate

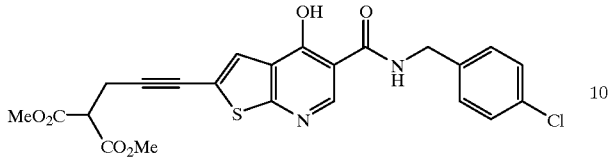

To a solution of N-(4-chlorobenzyl)4-hydroxy-2-iodothieno[2,3-b]pyridine-5-carboxamide (Example No. 2) (0.500 g) in diethylamine (14 mL) and DMF (1.5 mL) is added copper iodide (0.064 g) and $Pd(PPh_3)_2Cl_2$ (0.039 g) followed by addition of dimethyl propargyl malonate (0.24 mL). The reaction is stirred at rt for 18 h. The reaction mixture is concentrated in vacuo. The resulting orange solid is purified via column chromatography ($CH_2Cl_2$:$CH_3OH$; 98:2). Fractions homogeneous by TLC are combined and concentrated in vacuo to yield an orange solid which is recrystallized twice from methanol to yield 0.267 g (49%) of the title compound as an off-white solid.

Physical characteristics are as follows:

Mp 197–198° C.; $^1H$ NMR (300 MHz, DMSO-$d_6$) δ 13.30, 10.40, 8.74, 7.41–7.33, 4.54, 3.94, 3.71, 3.01; $^{13}C$ NMR (75 MHz, DMSO-$d_6$) δ 168.5, 139.0, 131.9, 129.6, 128.8, 126.6, 93.2, 74.8, 53.2, 50.3, 41.9, 19.6; IR (drift) 2353, 2327, 2229, 1738, 1663, 1646, 1593, 1568, 1540, 1516, 1491, 1435, 1347, 1286, 1240cm$^{-1}$; MS (FAB) m/z 487 (MH+, 99), 973 (7), 490 (12), 489 (43), 488 (37), 487 (99), 486 (21), 346 (27), 140 (13), 127 (14), 125 (4 1); HRMS (FAB) found 487.0714; Anal. Found: C, 56.46; H, 3.80; N, 5.74; Cl, 7.32; S, 6.55 (corrected for 3. 10% $H_2O$).

EXAMPLE 11

2-Bromo-N-(4-chlorobenzyl)-7-ethyl-4-oxo-4,7-dihydrothieno[2,3-b]pyridine-5-carboxamide

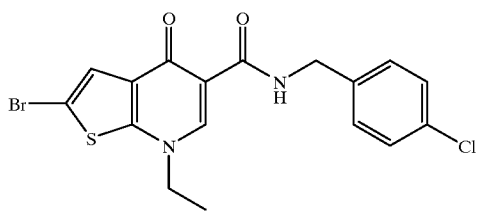

A mixture of ethyl 2-bromo-7-ethyl4-oxo-4,7-dihydrothieno[2,3-b]pyridine-5-carboxylate (Eur. J. Med. Chem. 1987, 22, 139) (0.500 g) and 4-chlorobenzylamine (1.84 mL) is stirred at 190° C. for 1 h. The reaction is then allowed to cool to rt and is diluted with toluene. The resulting precipitate is filtered off and washed with toluene followed by hexanes to yield a tan solid. This material is recrystallized from acetic acid/water then ethanol to yield 0.379 g (59%) of the title compound as a white, crystalline solid.

Physical characteristics are as follows:

Mp 196–197° C.; $^1H$ NMR (300 MHz, DMSO-$d_6$) δ 10.43, 8.76, 7.60, 7.41–7.33, 4.54,4.30, 1.43; $^{13}C$ NMR (75 MHz, DMSO-$d_6$) δ 171.4, 164.4, 150.2, 144.8, 139.0, 132.3, 131.9, 129.6, 128.8, 126.2, 115.5, 108.3, 52.3, 41.9, 14.3; IR (mull) 3083, 3043, 2407, 1930, 1650, 1593, 1543, 1515, 1501, 1494, 1441, 1416, 1411, 1232, 801 cm$^{-1}$; MS (ESI+) m/z 426 (M+H)$^+$; Anal. Found: C, 48.01; H, 3.59; N, 6.54; Br, 18.43; Cl, 8.20; S, 7.35.

EXAMPLE 12

N-(4-Chlorobenzyl)-7-ethyl-4-oxo-4,7-dihydrothieno[2,3-b]pyridine-5-carboxamide

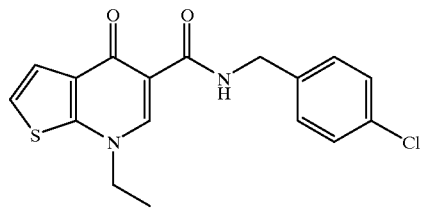

A mixture of ethyl 7-ethyl-4-oxo-4,7-dihydrothieno[2,3-b]pyridine-5-carboxylate (Eur. J. Med. Chem. 1987, 22, 139) (0.447 g) and 4-chlorobenzylamine (2.42 mL) is stirred at 190° C. for 1 h. The reaction is then allowed to cool to rt and is diluted with toluene. The resulting precipitate is filtered off and washed with toluene followed by hexanes to yield a pale yellow solid. This material is recrystallized from acetic acid/water then ethanol to yield 0.312 g (45%) of the title compound as a white solid.

Physical characteristics are as follows:

Mp 183–184° C.; $^1H$ NMR (300 MHz, DMSO-$d_6$) δ 10.57, 8.78, 7.53, 7.46, 7.41–7.33, 4.55, 4.35, 1.45; $^{13}C$ NMR (75 MHz, DMSO-$d_6$) δ 172.8, 164.8, 150.3, 144.9, 139.1, 132.0, 131.9, 129.6, 128.8, 123.3, 121.9, 115.0, 52.2, 41.9, 14.3; IR (mull) 3075, 1658, 1599, 1543, 1517, 1492, 1419, 1408, 1229, 1084, 1015, 808, 801, 714, 610 cm$^{-1}$; MS (ESI+) m/z 347 (M+H)$^+$; Anal. Found: C, 58.62; H, 4.48; N, 8.07; Cl, 10.10; S, 9.12.

EXAMPLE 13

N-(4-Chlorobenzyl)-7-ethyl-2-iodo-4-oxo-4,7-dihydrothieno[2,3-b]pyridine-5-carboxamide

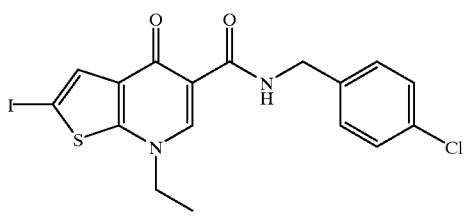

Carbonyldiimidazole (0.290 g) is added to a solution of 7-ethyl-2-iodo-4-oxo-4,7-dihydrothieno[2,3-b]pyridine-5-carboxylic acid (Eur. J. Med. Chem. 1987, 22, 139) (0.520 g) in DMF (13 mL). The reaction is heated to 60° C. and stirred for 18 h. The reaction mixture is cooled to rt, and 4-chlorobenzylamine (0.22 mL) is added. The reaction is stirred at rt for 7 h. The reaction mixture is poured into 20% aqueous HOAc (50 mL), and the resulting off-white solid is filtered off. This material is recrystallized twice from methanol to yield 0.372 g (53%) of the title compound as an off-white, crystalline solid.

Physical characteristics are as follows:

Mp 214–218° C.; $^1$H NMR (300 MHz, DMSO-d$_6$) δ 10.45, 8.72, 7.71, 7.41–7.33, 7.53, 4.30, 1.42; $^{13}$C NMR (75 MHz, TFA) δ 166.4, 165.9, 158.7, 141.5, 134.9, 133.1, 131.0, 129.7, 129.1, 129.0, 110.2, 108.8, 77.4, 56.0, 44.0, 12.4; IR (drift) 1654, 1590, 1541, 1511, 1489, 1431, 1408, 1295, 1217, 1086, 1014, 851, 800, 794, 707, cm$^{-1}$; MS (ESI+) m/z 473 (M+H)$^+$; Anal. Found: C, 42.80; H, 3.00; N, 5.82; Cl, 7.51; S, 6.85.

EXAMPLE 14

N-(4-Chlorobenzyl)-7-ethyl-2-(3-hydroxy-1-propynyl)-4-oxo4,7-dihydrothieno[2,3-b]pyridine-5-carboxamide

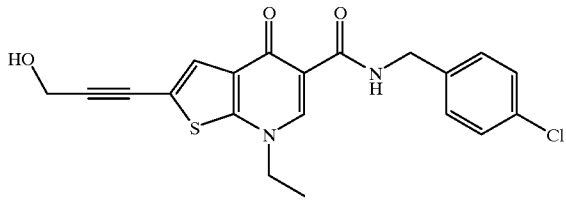

To a suspension of N-(4-chlorobenzyl)-7-ethyl-2-iodo4-oxo4,7-dihydro-thieno[2,3-b]pyridine-5-carboxamide (Example No. 12) (0.267 g) in diethylamine (14 mL) is added copper iodide (0.032 g) and Pd(PPh$_3$)$_2$Cl$_2$ (0.009 g) followed by addition of propargyl alcohol (39 mL). The reaction is stirred at rt for 18 h. The diethylamine is removed in vacuo, and the resulting residue is partitioned between H$_2$O (25 mL) and CH$_2$Cl$_2$ (25 mL). The organic layer is removed, and the aqueous layer is extracted with CH$_2$Cl$_2$ (3×25 mL). The combined organic layers are dried with MgSO$_4$, filtered, and concentrated in vacuo. The resulting orange solid is purified by column chromatography (CH$_2$Cl$_2$:CH$_3$OH, 98:2). Fractions homogeneous by TLC are combined and concentrated in vacuo to yield 0.158 g (70%) of the title compound as a yellow, crystalline solid.

Physical characteristics are as follows:

Mp 217–219° C.; $^1$H NMR (300 MHz, DMSO-d$_6$) δ 10.41, 8.79, 7.53, 7.41–7.33, 5.47, 4.54, 4.36, 4.29, 1.44; $^{13}$C NMR (75 MHz, DMSO-d$_6$) δ 172.3, 164.4, 149.7, 145.5, 138.9, 131.9, 131.5, 129.6, 128.8, 128.0, 116.9, 115.6, 96.9, 76.2, 52.4, 50.0, 41.9, 14.2; IR (drift) 3390, 2478, 2339, 2284, 2040, 1915, 1655, 1591, 1544, 1502, 1300, 1224, 1029, 1015, 795, cm$^{-1}$; MS (ESI+) m/z 399 (M+H)$^+$; Anal. Found: C, 59.42; H, 4.35; N, 6.88; Cl, 8.85; S, 7.98.

EXAMPLE 15

N-(4-Chlorobenzyl)-7-ethyl-2-(4-hydroxy-1-butynyl)-4-oxo-4,7-dihydrothieno[2,3-b]pyridine-5-carboxamide

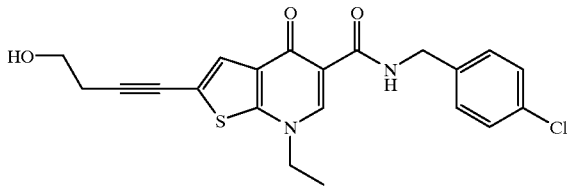

To a suspension of 2-bromo-N-(4-chlorobenzyl)-7-ethyl4-oxo-4,7-dihydro-thieno[2,3-b]pyridine-5-carboxamide (Example No. 11) (0.500 g) in diethylamine (12 mL) is added copper iodide (0.067 g) and Pd(PPh$_3$)$_2$Cl$_2$ (0.041 g) followed by addition of 3-butyn-1-ol (0.11 mL). The reaction is stirred at rt for 3 d. The diethylamine is removed in vacuo and the resulting residue is partitioned between H$_2$O (50 mL) and CH$_2$Cl$_2$ (50 mL). The organic layer is removed, and the aqueous layer is extracted with CH$_2$Cl$_2$ (3×50 mL). The combined organic layers are washed with a saturated NH4Cl solution (50 mL), dried with MgSO4, filtered, and concentrated in vacuo. The resulting orange solid is purified by column chromatography (CH$_2$Cl$_2$:CH$_3$OH, 98:2). Fractions homogeneous by TLC are combined and concentrated in vacuo. The resulting yellow solid is recrystallized from methanol to yield 0.312 g (64%) of the title compound as a pale yellow, crystalline solid.

Physical characteristics are as follows:

Mp 158–162° C.; $^1$H NMR (300 MHz, DMSO-d$_6$) δ 10.43, 8.78, 7.48, 7.41–7.33, 4.96, 4.55, 4.31, 3.60, 2.63, 1.43; $^{13}$C NMR (75 MHz, DMSO-d$_6$) δ 172.2, 164.4, 149.2, 145.3, 139.0, 131.9, 131.5, 129.6, 128.8, 127.1, 117.9, 115.5, 96.4, 73.5, 59.8, 52.4, 24.1, 14.2; IR (drift) 3050, 2223, 1921, 1653, 1593, 1549, 1545, 1502, 1389, 1298, 1230, 102, 1058, 799, 725 cm$^{-1}$; HRMS (EI) found 414.0800; Anal. Found: C, 60.70; H, 4.56; N, 6.77; Cl, 8.43; S, 7.59 (coffected for 0.75% H$_2$O).

EXAMPLE 16

N-(4-Chlorobenzyl)-7-ethyl-2-(3-hydroxypropyl)-4-oxo-4,7-dihydrothieno [2,3-b] pyfidine-5-carboxamide

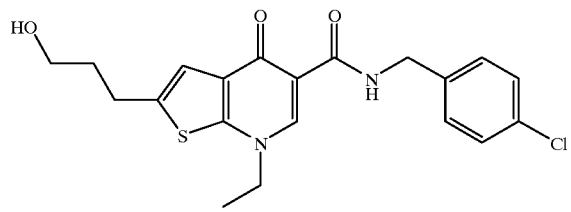

A solution of N-(4-chlorobenzyl)-7-ethyl-2-(3-hydroxy-1-propynyl)4-oxo-4,7-dihydrothieno[2,3-b]pyridine-5-carboxamide (Example No. 14) (0.197 g) in 1/1 CH$_2$Cl$_2$/CH$_3$OH (50 mL) is hydrogenated over 10% Pd/C (59 mg) at 35 psi for 2 h. The reaction mixture is filtered through a Celite pad, and the filtrate is concentrated in vacuo. The resulting yellow solid is purified via column chromatography (CH$_2$Cl$_2$, CH$_2$Cl$_2$:CH$_3$OH; 98:2, 95:5). Fractions homogeneous by TLC are combined and concentrated in vacuo to yield 0.114 g (57%) of the title compound as a white solid.

Physical characteristics are as follows:

Mp 144–146° C.; $^1$H NMR (300 MHz, DMSO-d$_6$) δ 10.62, 8.72, 7.41–7.33, 7.20, 4.56, 4.55, 4.31, 3.47, 2.90, 1.80, 1.44; $^{13}$C NMR (75 MHz, DMSO-d$_6$) δ 172.3, 164.8, 148.6, 144.2, 140.5, 139.1, 132.1, 131.8, 129.6, 128.8, 120.0, 115.1, 60.0, 52.1, 41.9, 34.3, 26.5, 14.4; IR (drift) 3055, 2929, 2352, 1916, 1654, 1594, 1551, 1544, 1507, 1491, 1299, 1230, 1092, 801, 708 cm$^{-1}$; MS (ESI–) for m/z 403 (M–H)$^-$; Anal. Found: C, 59.61; H, 5.38; N, 6.75; Cl, 8.51; S, 7.61.

EXAMPLE 17

N-(4-Chlorobenzyl)-7-(2-hydroxyethyl)-2-(3-hydroxy-1-5 propynyl)-4-oxo-4,7-dihydrothieno[2,3-b]pyridine-5-carboxamide

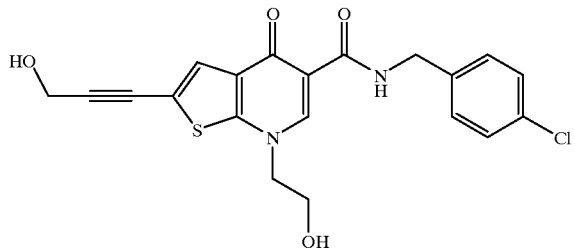

To a solution of N-(4chlorobenzyl)4-hydroxy-2-(3-hydroxy-1-propynyl)thieno[2,3-b]pyridine-5-carboxamide (Example No. 5) (0.250 g) in DMF (3 mL) is added K$_2$CO$_3$ (0.278 g) and 2-bromoethanol (0.14 mL). The reaction is heated to 100° C. and stirred for 18 h. The reaction mixture is concentrated in vacuo, and the resulting residue is partitioned between H$_2$O (50 mL) and CH$_2$Cl$_2$ (50 mL). The aqueous layer is extracted with CH$_2$Cl$_2$ (3×50 mL). The combined organic layers are dried with MgSO$_4$, filtered, and concentrated in vacuo to give a small amount of starting material. The desired product precipitates out of the aqueous layer as a tan solid. This material is recrystallized from methanol to yield 0.100 g (36%) of the title compound as a tan, crystalline solid.

Physical characteristics are as follows:

Mp 231–234° C. (dec); $^1$H NMR (300 MHz, DMSO-d$_6$) δ 10.43, 8.70, 7.56, 7.42–7.33, 5.46, 5.16, 4.55, 4.36, 4.31, 3.82; $^{13}$C NMR (75 MHz, DMSO-d$_6$) δ 174.4, 167.0, 152.9, 149.0, 114.3, 134.2, 133.8, 132.0, 131.2, 130.1, 119.1, 117.3, 99.1, 78.5, 62.1, 52.3, 44.2; IR (drift) 3381, 3228, 2395, 2218, 1905, 1646, 1591, 1555, 1505, 1341, 1079, 1026, 848, 800, 602 cm$^{-1}$; HRMS (EI) found 416.0596; Anal. Found: C, 56.62; H, 3.99; N, 6.52; Cl, 8.35; S, 7.52.

EXAMPLE 18

N-(4-Chlorobenzyl)-7-[2-(diethylamino)ethyl]-2-(3hydroxy-1-propynyl)4-oxo4,7-dihydrothieno[2,3-b]pyridine-5-carboxamide hydrochloride

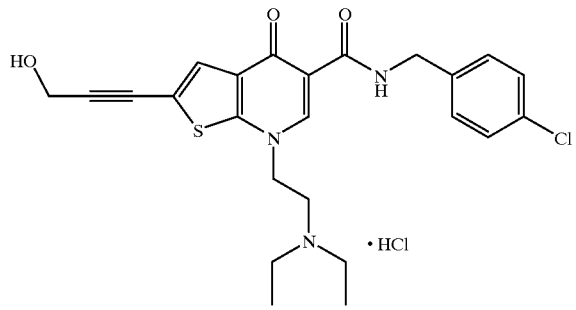

To a slution of N-(4-chlorobenzyi)-4-hydroxy-2-(3-hydroxy-1-propyny 2)thieno[2,3-b]pyridine-5-carboxamide (Example No. 5) (0.300 g) in DMF (4 mL) is added K$_2$CO$_3$ (0.334 g) and 2-bromo-N,N-diethylethyianmine hydrobromide (0.420 g). The reaction is heated to 90° C. After 4.5 h, an additional 0.111 g of K$_2$CO$_3$ is added and the reaction is stirred at 90° C. for 3 d. An additional 0.210 g of 2-bromo-N,N-diethylamine hydrobromide and 0.111 g of K$_2$CO$_3$ are added and the reaction is stiffed for an additional 5 h. The reaction mixture is added to H$_2$O and then concentrated in vacuo. The resulting brown solid is purified via column chromatography (CH$_2$Cl$_2$:CH$_3$OH; 98:2, 95:5). The resulting yellow solid is dissolved in methanolic HCl and concentrated in vacuo. The salt is recrystallized twice from ethanol to yield 0.080 g (20%) of the title compound as a pale yellow solid.

Physical characteristics are as follows:

Mp 212–214° C. (dec); $^1$H NMR (300 MHz, DMSO-d$_6$) δ 10.84, 10.36, 8.89, 7.58, 7.42–7.33, 5.50, 4.77, 4.56, 4.36, 3.60–3.54, 3.27–3.17, 1.26; $^{13}$C NMR (75 MHz, DMSO-d$_6$) δ 172.5, 164.2, 150.3, 146.7, 138.9, 131.9, 131.6, 129.6, 128.8, 127.9, 117.0, 115.8, 97.1, 76.1, 51.0, 50.0, 48.5, 47.1, 42.0, 40.8, 8.9; IR (drift) 3295, 3290, 2459, 2352, 2342, 1920, 1666, 1595, 1550, 1503, 1457, 1356, 1229, 1031, 798 cm$^{-1}$; MS (FAB) m/z 472 (MH$^+$); HRMS (FAB) found 472.1470; Anal. Found: C, 55.19; H, 5.32; N, 8.05; Cl, 13.74; S, 6.11.

EXAMPLE 19

2-[5-{[(4-Chlorobenzyl)amino]carbonyl}-2-(3-hydroxy-1-propynyl)4-oxothieno[2,3-b]pyridin-7(4H)-yl]acetic Acid

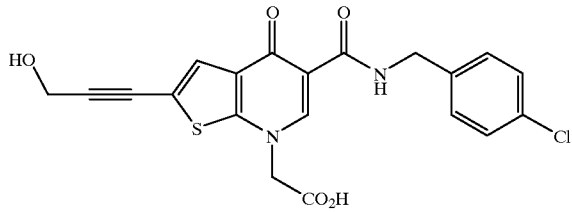

To a solution of N-(4-chlorobenzyl)4-hydroxy-2-(3-hydroxy-1-propynyl)-thieno[2,3-b]pyridine-5-carboxamide (Example No. 5) (0.250 g) in DMF (3 mL) is added K$_2$CO$_3$ (0.278 g) and bromoacetic acid (0.279 g). The reaction is heated to 100° C. and stirred for 18 h. An additional 0.200 g of bromoacetic acid is added and the reaction is stirred for an additional 18 h. The reaction mixture is concentrated in vacuo, and the resulting residue is dissolved in 10% NaOH and washed with $CH_2Cl_2$. The aqueous layer is acidified with conc. HCl and the resulting precipitate is filtered. This material is recrystallized 3 times from methanol to yield 0.068 g (24%) of the title compound as a tan solid.

Physical characteristics are as follows:

Mp 230–235° C. (dec); $^1$H NMR (300 MHz, DMSO-$d_6$) δ 13.85, 10.34, 8.83, 7.57, 7.42–7.33, 5.48, 5.45, 4.56, 4.34; $^{13}$C NMR (75 MHz, DMSO-$d_6$) δ 172.4, 168.5, 164.2, 150.9, 147.3, 138.9, 131.9, 131.1, 129.6, 128.9, 127.8, 116.9, 115.5, 97.0, 76.0, 57.0, 50.0, 42.0; IR (drift) 3362, 3279, 2342, 2223, 1726, 1639, 1581, 1551, 1505, 1416, 1243, 1222, 1208, 1027, 801 cm$^{-1}$; MS (FAB) m/z (rel. intensity) 431 (MH+, 99), 433 (39), 432 (26), 431 (99), 290 (20), 125 (34), 121 (21), 119 (13), 81 (11), 63 (23), 49 (24); HRMS (FAB) found 431.0474; Anal. Found: C, 52.52; H, 3.33; N, 6.08; Cl, 9.90; S, 7.10.

EXAMPLE 20

N-(4-Chlorobenzyl)-7-ethyl-2-(4-hydroxybutyl)4-oxo-4,7-dihydrothieno[2,3-b]pyridine-5-carboxamide

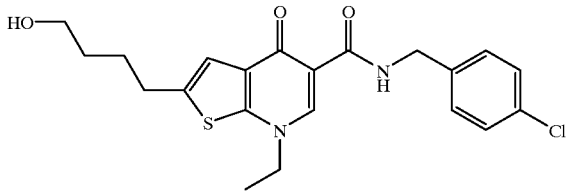

A solution of N-(4-chlorobenzyl)-7-ethyl-2-(4-hydroxy-1-butynyl)-4-oxo-4,7-dihydrothieno[2,3-b]pyridine-5-carboxamide (Example No. 15) (0.257 g) in 1/1 $CH_2Cl_2$/$CH_3OH$ (50 mL) is hydrogenated over 10% Pd/C (75 mg) at 35 psi for 2 h. The reaction mixture is filtered through a Celite pad, and the filtrate is concentrated in vacuo. The resulting pale yellow solid is purified via column chromatography ($CH_2Cl_2$:$CH_3OH$; 98:2). Fractions homogeneous by TLC are combined and concentrated in vacuo to yield 0.209 g (81%) of the title compound as a white solid.

Physical characteristics are as follows:

Mp 136–139° C.; $^1$H NMR (300 MHz, DMSO-$d_6$) δ 10.60, 8.72, 7.41–7.33, 7.20, 4.55, 4.42, 4.31, 3.44, 2.88, 1.69, 1.49, 1.44; $^{13}$C NMR (75 MHz, DMSO-$d_6$) δ 172.3, 164.8, 148.6, 144.1, 140.7, 139.1, 132.1, 131.8, 129.6, 128.8, 120.0, 115.1, 60.7, 52.1, 41.9, 32.2, 29.7, 27.8, 14.4; IR (drift) 3052, 2934, 1920, 1653, 1593, 1550, 1506, 1390, 1304, 1231, 1092, 1052, 801, 725, 710cm$^{-1}$; MS(ESI–)for m/z 417 (M–H)$^-$; Anal. Found: C, 60.26; H, 5.51; N, 6.73; Cl, 8.25; S, 7.43.

EXAMPLE 21

N-(4-Chlorobenzyl)-7-(2-hydroxyethyl)-2-(3-hydroxypropyl)4-oxo-4,7-dihydrothieno[2,3-b]pyridine-5-carboxamide

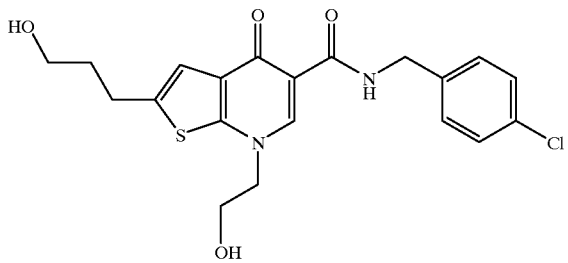

To a solution of N-(4-chlorobenzyl)-4-hydroxy-2-(3-hydroxypropyl)-thieno-[2,3-b]pyridine-5-carboxamide (Example No. 8) (0.330 g) in DMF (5 mL) are added $K_2CO_3$ (0.363 g) and 2-bromoethanol (0.19 mL). The reaction is heated to 100° C. and stirred for 18 h. An additional 0.19 mL of 2-bromoethanol is added and stirring is continued for 18 h. An additional 0.19 mL of 2-bromoethanol and 0.363 g of $K_2CO_3$ is added. After 5 h, 35 mg of NaH (60% oil dispersion) is added. The reaction is stirred for 1 h. The reaction mixture is cooled to rt and concentrated in vacuo. The residue is suspended in $CH_2Cl_2$ and $H_2O$. The resulting off-white precipitate is filtered off and purified via column chromatography ($CH_2Cl_2$:$CH_3OH$; 98:2, 95:5). Fractions homogeneous by TLC are combined and concentrated in vacuo to yield 0.145 g (39%) of the title compound as a white solid.

Physical characteristics are as follows:
Mp 174–178° C.; $^1$H NMR (300 MHz, DMSO-$d_6$) δ 10.62, 8.63, 7.41–7.33, 7.19, 5.14, 4.58–4.53, 4.29, 3.81, 3.47, 2.90, 1.79; $^{13}$C NMR (75 MHz, DMSO-$d_6$) δ 172.4, 164.9, 149.2, 145.5, 140.2, 139.1, 132.0, 131.9, 129.6, 128.8, 119.9, 114.4, 60.0, 59.4, 58.7, 41.9, 34.3, 26.4; IR (drift) 3282, 3265, 2480, 1657, 1648, 1599, 1550, 1524, 1493, 1304, 1220, 1090, 1057, 1014, 798 cm$^{-1}$; MS (ESI–) for m/z 419 (M–H)$^-$; Anal. Found: C, 56.84; H, 5.01; N, 6.53; Cl, 8.33; S, 7.47.

EXAMPLE 22

N-(4-Chlorobenzyl)-7-[2-(diethylamino)ethyl]-2-(3-hydroxypropyl)4-oxo4,7-dihydrothieno[2,3-b]pyridine-5-carboxamide Hydrorhloride

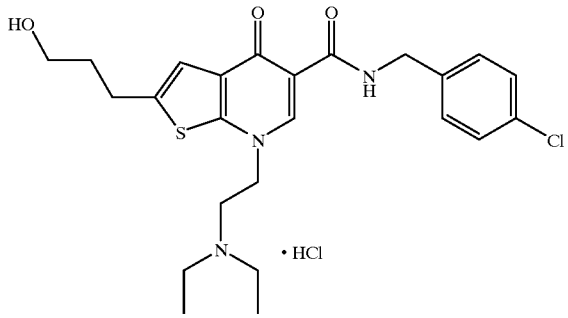

To a solution of N-(4-chlorobenzyl)4-hydroxy-2-(3-hydroxypropyl)thieno[2,3-b]pyridine-5-carboxamide (Example No. 8) (0.300 g) in DMF (4 mL) are added K$_2$CO$_3$ (0.550 g) and 2-bromo-N,N-diethylethylamine hydrobromide (0.623 g). The reaction is heated to 90° C. and stirred for 3 d. An additional 0.220 g of K$_2$CO$_3$ and 0.415 g of 2-bromo-N,N-diethylethylamine hydrobromide are added. The reaction is stirred at 90° C. for 6 h. The reaction mixture is concentrated in vacuo, and the resulting residue is partitioned between CH$_2$Cl$_2$ (25 mL) and H$_2$O (25 mL). The aqueous layer is extracted with CH$_2$Cl$_2$ (3×25 mL). The combined organic layers are dried with MgSO$_4$, filtered and concentrated in vacuo. The resulting yellow oil is purified via column chromatography (CH$_2$Cl$_2$:CH$_3$OH; 98:2, 95:5). Fractions homogeneous by TLC are combined and concentrated in vacuo to yield a yellow oil. This material is dissolved in methanolic HCl and then concentrated in vacuo. The residue is recrystallized twice from ethyl acetate/methanol to yield 0.078 g (19%) of the title compound as an off-white, crystalline solid.

Physical characteristics are as follows:

Mp 111–114° C.; $^1$H NMR (300 MHz, DMSO-d$_6$) δ 10.93, 10.53, 8.82, 7.42–7.33, 7.21, 4.76,4.56, 3.55, 3.42, 3.22, 2.92, 1.83, 1.28; $^{13}$C NMR (75 MHz, DMSO-d$_6$) δ 172.5, 164.6, 149.0, 145.5, 140.6, 139.1, 132.1, 131.9, 129.6, 128.8, 120.2, 115.4, 60.0, 50.7, 48.7, 47.2, 41.9, 34.4, 26.5, 8.9; IR (drift) 2350, 2350, 2338, 2329, 2250, 1941, 1656, 1596, 1537, 1507, 1489, 1459, 1451, 1011, 799 cm$^{-1}$; MS (FAB) m/z 476 (MH+); HRMS (FAB) found 476.1792; Anal. Found: C, 55.44; H, 6.27; N, 8.01; Cl, 13.90; S, 6.24 (corrected for 6.35% H$_2$O).

EXAMPLE 23

N-(4-Chlorobenzyl)-2-iodo-7-methyl-4-oxo-4,7-dihydrothieno[2,3-b]pyridine-5-carboxamide

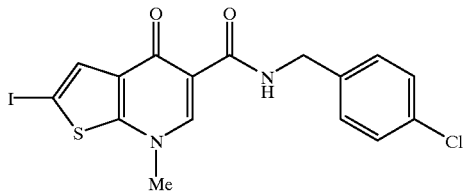

To a solution of N-(4-chlorobenzyl)4-hydrgxy-2-iodothieno-[2,3-b]pyridine-5-carboxamide (Example No. 2) (2.00 g) in DMF (14 mL) are added K$_2$CO$_3$ (1.76 g) and iodomethane (0.79 mL). The reaction is heated to 90° C. and stirred for 18 h. The reaction mixture is concentrated in vacuo. The resulting residue is partitioned between H$_2$O (100 mmL) and CH$_2$Cl$_2$ (200 mL). The aqueous layer is extracted with CH$_2$Cl$_2$ (3×150 mL). The combined organic layers are dried with MgSO$_4$, filtered, and concentrated in vacuo. The resulting off-white solid is recrystallized from ethanol to yield 1.78 g (92%) of the title compound as an off-white solid.

Physical characteristics are as follows:

Mp 236–237° C.; $^1$H NMR (300 MHz, DMSO-d$_6$) δ 10.45, 8.69, 7.71, 7.41–7.32, 4.54, 3.93; $^{13}$C NMR (75 MHz, DMSO-d$_6$) δ 171.1, 164.5, 154.8, 145.9, 139.0, 133.2, 132.5, 131.9, 129.6, 128.8, 115.0, 73.5, 43.5, 41.9; IR (drift) 3042, 1916, 1648, 1595, 1545, 1514, 1492, 1426, 1361, 1340, 1305, 1242, 1172, 1123, 798 cm$^{-1}$; MS (ESI+) for m/z 459 (M+H)+; Anal. Found: C, 41.65; H, 2.63; N, 6.17; Cl, 7.76; S, 6.96.

EXAMPLE 24

N-(4-Chlorobenzyl)-2-(3-hydroxy-1-propynyl)-7-methyl-4-oxo-4,7-dihydrothieno[2,3-b]pyridine-5-carboxamide

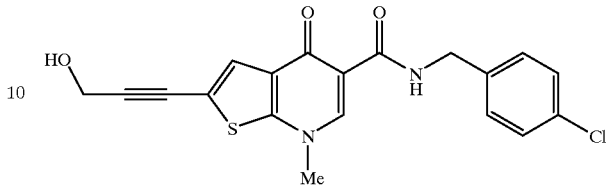

To a suspension of N-(4-chlorobenzyl)-2-iodo-7-methyl-4-oxo-4,7-dihydro-thieno[2,3-b]pyridine-5-carboxamide (Example No. 23) (1.632 g) in diethylamnine (40 mL) is added copper iodide (0.210 g) and Pd(PPh$_3$)$_2$Cl$_2$ (0.125 g) followed by addition of propargyl alcohol (0.29 mL). The reaction is stirred at rt for 18 h. The diethylamine is removed in vacuo and the resulting brown solid is purified via column chromatography (CH$_2$Cl$_2$:CH$_3$OH; 98:2). Fractions homogeneous by TLC are combined and concentrated in vacuo to yield an orange solid which is recrystallized from ethanol to yield 1.06 g (77%) of the title compound as a yellow solid.

Physical characteristics are as follows:

Mp 206–208° C.; $^1$H NMR (300 MHz, DMSO-d$_6$) δ 10.42, 8.76, 7.57, 7.41–7.33, 5.47, 4.55, 4.37, 3.95; $^{13}$C NMR (75 MHz, DMSO-d$_6$) δ 172.2, 164.4, 151.0, 146.8, 138.9, 131.9, 130.9, 129.6, 128.8, 128.0, 116.9, 115.2, 96.8, 76.2, 50.0, 43.6, 41.9; IR (drift) 3378, 3222, 3058, 1651, 1593, 1550, 1544, 1509, 1410, 1349, 1305, 1243, 1026, 799, 714 cm$^{-1}$; MS (FAB) m/z 387 (MH$^+$); HRMS (FAB) found 387.0558; Anal. Found: C, 58.79; H, 3.99; N, 7.28; Cl, 9.26; S, 7.98 (corrected for 1.53% H$_2$O).

EXAMPLE 25

N-(4-Chlorobenzyl)-2-(3-hydroxypropyl)-7-methyl4-oxo-4,7-7dihydrothieno[2,3-b]pyridine-5-carboxamide

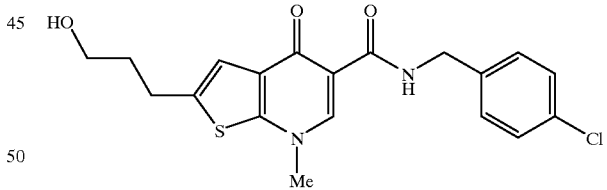

A solution of N-(4-chlorobenzyl)-2-(3-hydroxy-1-propynyl)-7-methyl-4-oxo-4,7-dihydrothieno[2,3-b] pyridine-5-carboxamide (Example No. 24) (0.520 g) in 1/1 CH$_2$Cl$_2$/ethanol (160 mL) is hydrogenated over 10% Pd/C (0.156 g) at 35 psi for 2 h. The reaction mixture is filtered through a Celite pad, and the filtrate is concentrated in vacuo. The resulting pale yellow solid is purified via column chromatography (CH$_2$Cl$_2$:CH$_3$OH; 98:2). Fractions homogeneous by TLC are combined and concentrated in vacuo to yield a pale yellow solid (this material contains a small amount of partially reduced product). This material is dissolved in ethanol (100 mL) and hydrogenated over 10% Pd/C (0.156 g) at 35 psi for 1 h. The reaction mixture is filtered through a Celite pad, and the filtrate is concentrated in vacuo. The resulting off-white solid is recrystallized from ethanol to yield 0.211 g (40%) of the desired product as an off-white solid.

Physical characteristics are as follows:

Mp 197–198° C.; $^1$H NMR (300 MHz, DMSO-d$_6$) δ 10.61, 8.69, 7.41–7.33, 7.21, 4.58–4.53, 3.95, 3.47, 2.91, 1.80; $^{13}$C NMR (75 MHz, DMSO-d$_6$) δ 172.2, 164.9, 149.8, 145.5, 140.6, 139.1, 131.8, 131.5, 129.6, 128.8, 120.0, 114.7, 60.0, 43.4, 41.9, 34.4, 26.5; IR (drift) 3052, 1921, 1653, 1596, 1557, 1512, 1489, 1429, 1305, 1242, 1091, 1032, 801, 727, 712 cm$^{-1}$; HRMS (FAB) found 391.0904; Anal. Found: C, 57.42; H, 4.78; N, 7.03; Cl, 8.78; S, 8.13.

EXAMPLE 26

N-(4-Chlorobenzyl)-2-iodo-7-isopropyl-4-oxo-7-3dihydrothiedion[2,3-b]pyridine-5-carboxamide

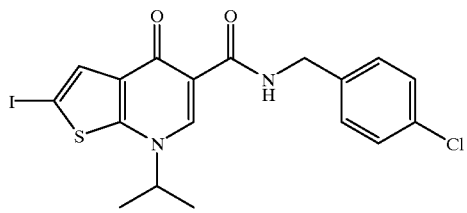

To a solution of N-(4-chlorobenzyl)-4-hydroxy-2-iodothieno-[2,3-b]pyridine-5-carboxamide (Example No. 2) (2.00 g) in DMF (14 mL) are added K$_2$CO$_3$ (1.76 g) and 2-bromopropane (1.19 mL). The reaction is heated to 90° C. and stirred for 18 h. The reaction mixture is concentrated in vacuo. The resulting residue is partitioned between H$_2$O (100 mL) and CH$_2$Cl$_2$ (200 mL). The aqueous layer is extracted with CH$_2$Cl$_2$ (3×150 mL). The combined organic layers are dried with MgSO$_4$, filtered and concentrated in vacuo. The resulting yellow solid is purified via column chromatography (CH$_2$Cl$_2$, CH$_2$Cl$_2$:CH$_3$OH; 99:1). Fractions homogeneous by TLC are combined and concentrated in vacuo to yield a yellow solid. This material is recrystallized from ethanol then methanol to yield 0.808 g (39%) of the title compound as an off-white solid.

Physical characteristics are as follows:

Mp 173–180° C.; $^1$H NMR (300 MHz, DMSO-d$_6$) δ 10.45, 8.65, 7.71, 7.41–7.33, 4.54, 4.49, 1.56; $^{13}$C NMR (75 MHz, DMSO-d$_6$) δ 171.2, 164.4, 153.6, 140.5, 139.0, 133.9, 132.5, 131.9, 129.7, 128.8, 115.5, 73.8, 59.5,42.0, 21.4; IR (drift) 2975, 1905, 1661, 1587, 1541, 1492, 1463, 1436, 1338, 1319, 1280, 1223, 1209, 1193, 794 cm$^{-1}$; MS (ESI+) for m/z 487 (M+H)$^+$; Anal. Found: C, 44.36; H, 3.21; N, 5.76; Cl, 7.31; S, 6.55.

EXAMPLE 27

N-(4-Chlorobenzyl)-2-(3-hydroxy-1-propynyl)-7-isopropyl-4-oxo-4,7-dihydrothieno[2,3-b]pyridine-5-carboxamide

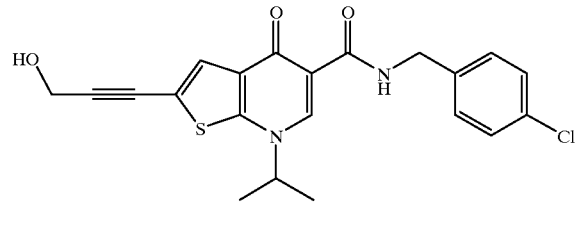

To a suspension of N-(4-chlorobenzyl)-2-iodo-7-isopropyl4-oxo4,7-dihydrothieno[2,3-b]pyridine-5-carboxamnide (Example No. 26) (0.717 g) in diethylamine (20) is added copper iodide (0.084 g) and Pd(PPh$_3$)$_2$Cl$_2$ (0.052 g) followed by addition of propargyl alcohol (0.12 mL). The reaction is stirred at rt for 18 h. The diethylamine is removed in vacuo and the resulting brown solid is purified via column chromatography (CH$_2$Cl$_2$:CH$_3$OH; 98:2). Fractions homogeneous by TLC are combined and concentrated in vacuo to yield an orange solid which is recrystallized from ethanol then methanol to yield 0.281 g (46%) of the title compound as a yellow, crystalline solid.

Physical characteristics are as follows:

Mp 190–196 C; $^1$H NMR (300 MHz, DMSOA6) δ 10.42, 8.71, 7.56, 7.41–7.33, 5.47, 4.54, 4.51, 4.37, 3.95, 1.57; $^{13}$C NMR (75 MHz, DMSO-d$_6$) δ 172.2, 164.3, 149.7, 141.2, 140.6, 138.9, 131.9, 131.6, 129.7, 128.8, 128.0, 123.3, 121.8, 116.9, 115.7, 96.9, 76.1, 59.5, 50.0, 42.0, 21.4; IR (drift) 3450, 2320, 2229, 2059, 1908, 1657, 1591, 1550, 1500, 1291, 1218, 1203, 1045, 803, 795 cm$^{-1}$; MS (ESI+) for m/z 415 (M+H)$^+$; Anal. Found: C, 60.47; H, 4.50; N, 6.55; Cl, 8.47; S, 7.73.

EXAMPLE 28

N-(4-Chlorobenzyl)-2-(3-hydroxypropyl)-7-isopropyl-4-oxo4,7-dihydrothieno[2,3-b]pyridine-5-carboxamide

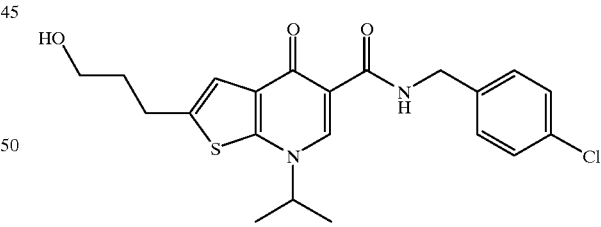

A solution of N-(4-chlorobenzyl)-2-(3-hydroxy-1-propynyl)-7-isopropyl-4-oxo4,7-dihydrothieno[2,3-b]pyridine-5-carhoxamide (Example No. 27) (0.225 g) in ethanol (50 mL) is hydrogenated over 10% Pd/C (68 mg) at 35 psi for 2 h. The reaction mixture is filtered through a Celite pad, and the filtrate is concentrated in vacuo. The resulting pale yellow solid is recrystallized from ethyl acetate/heptane to yield 0.104 g (46%) of the desired product as an off-white solid.

Physical characteristics are as follows:

Mp 84–92° C.; $^1$H NMR (300 MHz, DMSO-d$_6$) δ 10.61, 8.66, 7.41–7.33, 7.21, 4.59–4.50, 3.47, 2.91, 1.80, 1.57; $^{13}$C

NMR (75 MHz, DMSO-$d_6$) δ 172.2, 164.8, 148.6, 140.4, 140.0, 139.1, 132.2, 131.9, 129.7, 128.8, 120.0, 115.1, 60.0, 59.0, 41.9, 34.3, 26.4, 21.5; IR (drift) 3491, 1660, 1594, 1538, 1504, 1465, 1448, 1349, 1325, 1294, 1216, 1090, 1060, 1012, 798 cm$^{-1}$; MS (FAB) m/z 419 (MH$^+$); HRMS (FAB) found 419.1172; Anal. Found: C, 60.06; H, 5.52; N, 6.58; Cl, 8.27; S, 7.57.

EXAMPLE 29

4-{[3-(5-{[(4-Chlorobenzyl)amino]carbonyl}-7-ethyl-4-oxo-4,7-dihydrothieno[2,3-b]pyridin-2-yl)-2-propynyl]oxy}-4-oxobutanoic Acid

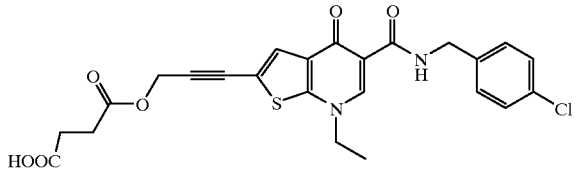

To a solution of N-(4-chlorobenzyl)-7-ethyl-2-(3-hydroxy-1-propynyl)-4-oxo-4,7-dihydrothieno[2,3-b]pyridine-5-carboxamide (Example No. 14) (0.200 g) in pyridine (10 mL) is added succinic anhydride (0.639 g). The reaction is stirred at rt for 18 h then at 40° C. for 1 h. The reaction mixture is concentrated in vacuo. The residue is suspended in H$_2$O (25 mL) and stirred for 1 h. An off-white solid is filtered off and recrystallized from ethanol to yield 0.210 g (84%) of the title compound as a pale yellow, crystalline solid.

Physical characteristics are as follows:

Mp 180–182° C.; $^1$H NMR (300 MHz, DMSO-$d_6$) δ 12.27, 10.38, 8.80, 7.65, 7.41–7.33, 5.02, 4.54, 4.31, 2.62–2.50, 1.44; $^{13}$C NMR (75 MHz, DMSO-$d_6$) δ 173.7, 172.3, 172.0, 164.3, 150.1, 145.6, 138.9, 131.9, 131.4, 129.6, 129.3, 128.8, 115.7, 91.0, 78.2, 52.8, 52.4, 42.0, 29.1, 29.0, 14.2; IR (drift) 2233, 1927, 1728, 1698, 1651, 1590, 1546, 1503, 1348, 1325, 1307, 1230, 1211, 1172, 801 cm$^{-1}$; MS (ESI–) for m/z 499 (M–H)$^-$; Anal. Found: C, 57.27; H, 4.40; N, 5.64; Cl, 7.04; S, 6.35.

EXAMPLE 30

3-(5-{[(4-Chlorobenzyl)amino]carbonyl}-7-ethyl-4-oxo-4,7-dihydrothieno[2,3-b]pyridin-2-yl)-2-propynyl 2-(4-Morpholinyl)acetate

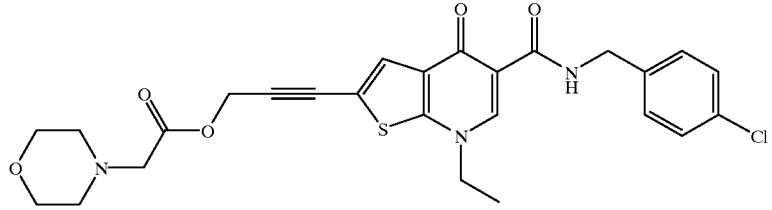

To a suspension of N-(4-chlorobenzyl)-7-ethyl-2-(3-hydroxy-1-propynyl)-4-oxo-4,7-dihydrothieno[2,3-b]pyridine-5-carboxamide (Example No. 14) (0.300 g) in CH$_2$Cl$_2$ (3 mL) at 0° C. is added pyridine (67 μL) followed by dropwise addition of bromoacetyl bromide (72 μL). The reaction is allowed to warm to rt. After stirring for 2 h at rt, an additional 67 μL of pyridine and 72 μL of bromoacetyl bromide are added. The reaction is stirred at rt for 30 min. The reaction mixture is diluted with CH$_2$Cl$_2$ (25 mL) and extracted with H$_2$O (2×25 mL). The organic layer is dried with MgSO$_4$, filtered, and concentrated in vacuo. The resulting yellow solid is recrystallized from methanol to yield 0.314 g (80%) of the bromide. This material (0.250 g) is dissolved in acetonitrile (5 mL) and CH$_2$Cl$_2$ (2 mL). Morpholine (0.10 mL) is added and the reaction is stirred at rt for 1 h. The reaction mixture is concentrated in vacuo. The resulting residue is dissolved in CH$_2$Cl$_2$ (70 mL) and washed with H$_2$O (2×70 mL) and brine (70 mL), dried with MgSO$_4$, filtered, and concentrated in vacuo. The resulting yellow solid is recrystallized from methanol to yield 0.183 g (72%) of the title compound as a pale yellow, crystalline solid.

Physical characteristics are as follows:

Mp 168–170° C.; $^1$H NMR (300 MHz, DMSO-$d_6$) δ 10.45, 8.67, 7.69, 7.33–7.27, 4.99, 4.63, 4.16, 3.78, 3.33, 1.60; $^{13}$C NMR (75 MHz, CDCl$_3$) δ 172.8, 168.8, 164.6, 149.6, 144.1, 137.2, 132.9, 131.8, 129.7, 129.0, 128.7, 116.3, 116.0, 89.1, 78.7, 66.5, 59.0, 53.1, 52.8, 52.4, 42.6, 14.1; IR (drift) 2229, 1921, 1730, 1655, 1596, 1543, 1500, 1348, 1228, 1192, 1175, 1133, 1112, 1011, 799 cm$^{-1}$; MS (ESI+) for m/z 528 (M+H)$^+$; Anal. Found: C, 59.07; H, 4.90; N, 7.86; Cl, 6.72; S, 6.08.

EXAMPLE 31

3-(5-{[(4-Chlorobenzyl)amino]carbonyl}-7-ethyl-4-oxo-4,7-dihydrothieno[2,3-b]pyridin-2-yl)-2-propynyl 2-Amino-3-methylbutanoate Hydrochloride

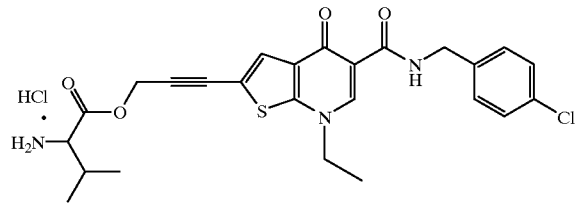

To a solution of N-(4-chlorobenzyl)-7-ethyl-2-(3-hydroxy-1-propynyl)-4-oxo-4,7-dihydrothieno[2,3-b]pyridine-5-carboxamide (Example No. 14) (0.400 g) in pyridine (16 mL) are added EDC (0.288 g), DMAP (0.020 g), and N-Boc valine (0.326 g). The reaction is stirred at rt for 3 d. The reaction mixture was concentrated in vacuo. The residue is dissolved in CH$_2$Cl$_2$ (80 mL), washed with H$_2$O (40 mL) and brine (40 mL), dried with MgSO$_4$, filtered, and concentrated in vacuo. The resulting yellow solid is recrystallized from ethanol to yield 0.492 g (82%) of the Boc-protected compound. This material (0.303 g) is dissolved in CH$_2$Cl$_2$ (6 mL) and cooled to 0° C. Trifluoroacetic acid (6 mL) is added, and the reaction is stirred at 0° C. for 1 h. The reaction mixture is concentrated in vacuo. The resulting residue is dissolved in CH$_2$Cl$_2$ (60 mL), washed with saturated aqueous NaHCO$_3$ (60 mL) and H$_2$O (60 mL), dried with MgSO$_4$, filtered, and concentrated in vacuo. The resulting white solid is recrystallized from ethanol to yield 0.128 g (51%) of the free amine as a white, crystalline solid. The amine (0.105 g) is dissolved in methanolic HCl (4 mL) and concentrated in vacuo. The resulting residue is recrystallized from methanol/ethyl acetate to yield 0.092 g (81%) of the title compound as a white solid.

Physical characteristics are as follows:

Mp 171–172° C.; $^1$H NMR (300 MHz, DMSO-d$_6$) δ 10.36, 8.81, 8.52, 7.66, 7.42–7.33, 5.22, 4.55, 4.33, 4.02, 2.22, 1.44, 1.01; $^{13}$C NMR (75 MHz, DMSO-d$_6$) δ 172.3, 169.0, 164.2, 150.3, 145.8, 138.9, 131.9, 131.3, 129.6, 129.5, 128.8, 115.7, 115.3, 90.1, 79.0, 57.6, 54.1, 52.5, 42.0, 30.0, 18.7, 18.0, 14.2; IR (drift) 3047, 2968, 2935, 2914, 2879, 2226, 1931, 1754, 1649, 1594, 1544, 1502, 1232, 1212, 803 cm$^{-1}$; MS (FAB) m/z 500 (MH$^+$); HRMS (FAB) found 500.1408; Anal. Found: C, 54.10; H, 5.06; N, 7.55; Cl, 12.77; S, 5.81.

EXAMPLE 32

3-(5-{[(4-Chlorobenzyl)amino]carbonyl}-7-ethyl-4-oxo-4,7-dihydrothieno[2,3-b]pyridin-2-yl)-2-propynyl 3-(4-Morpholinylmethyl)benzoate

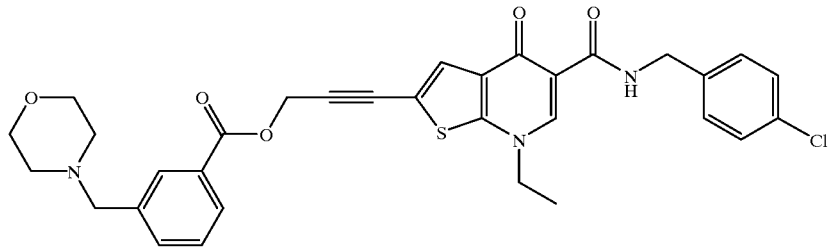

To a solution of N-(4-chlorobenzyl)-7-ethyl-2-(3-hydroxy-1-propynyl)-4-oxo-4,7-dihydrothieno[2,3-b]pyridine-5-carboxamide (Example No. 14) (0.956 g) in CH$_2$Cl$_2$ (15 mL) and triethylamine (0.73 mL) is added 3-chloromethylbenzoyl chloride (0.74 mL). The reaction is stirred at rt for 18 h. The reaction mixture is concentrated in vacuo. The resulting residue is partitioned between H$_2$O (80 mL) and CH$_2$Cl$_2$ (80 mL). The aqueous layer is extracted with CH$_2$Cl$_2$ (3×80 mL). The combined organic layers are dried with MgSO$_4$, filtered, and concentrated in vacuo. The resulting yellow oil is purified via column chromatography (CH$_2$Cl$_2$, CH$_2$Cl$_2$:CH$_3$OH, 98:2). The resulting yellow solid is recrystallized from ethyl acetate to yield 0.797 g (61%) of the chloride as a pale yellow solid. This material (0.400 g) is suspended in DMF (6 mL), and K$_2$CO$_3$ (0.300 g) and morpholine (0.19 mL) are added. The reaction is heated to 90° C. and stirred for 2 h. The reaction mixture is cooled to rt and concentrated in vacuo. The resulting residue is partitioned between H$_2$O (80 MnL) and CH$_2$Cl$_2$ (80 mL). Brine (50 mL) is added to break up the emulsion that forms. The aqueous layer is extracted with CH$_2$Cl$_2$ (3×80 mL). The combined organic layers are dried with MgSO$_4$, filtered, and concentrated in vacuo. The resulting pale yellow solid is recrystallized from ethanol to yield 0.346 g (79%) of the title compound as a pale yellow solid.

Physical characteristics are as follows:

Mp 147–150° C.; $^1$H NMR (300 MHz, DMSO-d$_6$) δ 10.38, 8.80, 7.95–7.89, 7.69, 7.64, 7.52, 7.41–7.33, 5.29, 4.55, 4.323.59–3.54, 2.36, 1.44; $^{13}$C NMR (75 MHz, DMSO-d$_6$) δ 172.3, 165.5, 164.3, 150.2, 145.7, 138.9, 134.9, 131.9, 131.4, 130.2, 129.6, 129.5, 129.4, 128.8, 128.7, 115.7, 115.6, 91.0, 78.5, 66.6, 62.2, 53.5, 52.4, 41.9, 14.1; IR (drift) 2228, 1926, 1726, 1651, 1591, 1542, 1500, 1300, 1278, 1248, 1189, 1118, 1081, 800, 743 cm$^{-1}$; MS (ESI+) for m/z 604 (M+H)$^+$. Anal. Found: C, 63.41; H, 4.89; N, 6.88; Cl, 5.97; S, 5.32.

EXAMPLE 33

Methyl 5-{[(4-Chlorobenzyl)amino]carbonyl}-4-hydroxythieno[2,3-b]pyridine-2-carboxylate

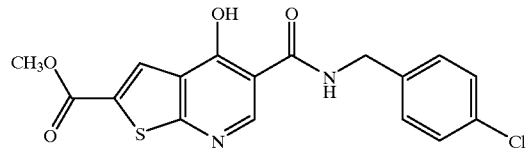

To a solution of N-(4-chlorobenzyl)-4-hydroxy-2-iodothieno[2,3-b]pyridine-5-carboxamide (2.61 g) from Example No. 2 in DMF (33 mL) are added triethylamine (1.6 mL), methanol (9.5 mL), Pd(OAc)$_2$(0.132 g), and dppp (0.242 g). Carbon monoxide is bubbled through the solution, and the reaction is heated to 70° C. The reaction is stirred at 70° C. for 18 h. The reaction mixture is cooled to rt, and water (25 mL) and 2 N HCl (25 mL) are added. The resulting precipitate is filtered off and purified by column chromatography (CH$_2$Cl$_2$; CH$_2$Cl$_2$/methanol, 99/1; 98/2). A mixture of starting material and desired product is isolated as a yellow solid. This material is re-subjected to the reaction conditions above. The reaction is stirred at 70° C. for 18 h. The reaction is cooled to rt and water (25 mL) and 2 N HCl (25 mL) are added. The resulting orange solid is filtered off and purified by column chromatography (CH$_2$Cl$_2$; CH$_2$Cl$_2$/methanol, 99/1; 98/2). Fractions homogeneous by TLC are combined and concentrated in vacuo to yield a pale yellow solid which is recrystallized from methanol to yield 1.337 g (60%) of the title compound as a pale yellow, crystalline solid.

Physical characteristics are as follows:

Mp 238–240° C.; $^1$H NMR (300 MHz, DMSO-d$_6$) δ 13.45, 10.30, 8.80, 7.96, 7.41–7.33, 4.55, 3.87; $^{13}$C NMR (75 MHz, DMSO-d$_6$) δ 173.3, 164.1, 161.7, 151.4, 143.5, 138.5, 131.4, 130.6, 129.1, 128.3, 127.9, 126.4, 114.0, 52.7, 41.4; IR (drift) 2944, 2350 (w), 1729, 1645, 1595, 1549, 1543, 1485, 1478, 1433, 1284, 1238, 1175, 800, 751 cm$^{-1}$; MS (ESI−) for m/z 375 (M−H)$^−$. Anal. Found (corrected for 3.64% H$_2$O): C, 54.03; H, 3.38; N, 7.39; Cl, 9.41; S, 8.52.

EXAMPLE 34

N-(4-Chlorobenzyl)-4-hydroxy-2-(hydroxymethyl)thieno[2,3-b]pyridine-5-carboxamide

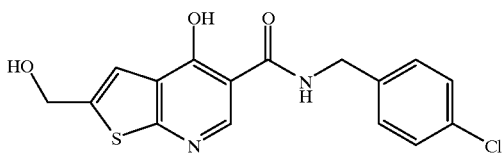

Methyl 5-{[(4-chlorobenzyl)amino]carbonyl}-4-hydroxythieno[2,3-b]pyridine-2-carboxylate (0.506 g) from Example No. 33 is dissolved in THF (100 mL) with heating and then the reaction is cooled in an ice bath. To this solution is added a 1.0 M solution of LiAlH4 in THF (2.4 mL). The reaction is allowed to warm to room temperature and is stirred for 2.5 h. The reaction is quenched with water (1 mL), 10% NaOH (1 mL), and H$_2$O (1 mL). The aluminum salts are filtered off and the filtrate is concentrated in vacuo. The resulting yellow oil is purified by column chromatography (CH$_2$Cl$_2$/methanol, 98/2; 95/5). Fractions homogeneous by TLC are combined and concentrated in vacuo to yield 0.254 g (54%) of the title compound as a pale yellow solid.

Physical characteristics are as follows:

Mp 205–210° C.; $^1$H NMR (300 MHz, DMSO-d$_6$) δ 13.34, 10.57, 8.66, 7.41–7.33, 7.22, 5.69, 4.68, 4.54; $^{13}$C NMR (75 MHz, DMSO-d$_6$) δ 172.4, 164.9, 148.5, 141.8, 141.4, 138.6, 131.4, 130.5, 129.2, 128.3, 117.3, 113.2, 58.5, 48.6, 41.4; IR (drift) 3007, 2917, 2854, 2319, 1903, 1647, 1593, 1568, 1538, 1511, 1493, 1353, 1298, 1123, 789 cm$^{-1}$; MS (ESI–) for m/z 347 (M–H)$^-$. Anal. Found: C, 54.86; H, 3.89; N, 7.86; Cl, 10.00; S, 9.01.

EXAMPLE 35

N-(4-Chlorobenzyl)-2-(hydroxymethyl)-7-methyl-4-oxo-4,7-dihydrothieno[2,3-b]pyridine-5-carboxamide

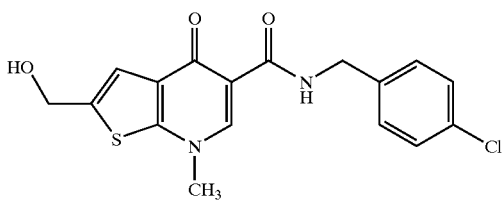

To a solution of N-(4-chlorobenzyl)-4-hydroxy-2-(hydroxymethyl)thieno[2,3-b]pyridine-5-carboxamide (0.955 g) from Example No. 34 in DMF (20 mL) is added potassium carbonate (0.567 g) followed by iodomethane (0.20 mL). The reaction is stirred at rt for 1 h. The reaction mixture is partitioned between water (50 mL) and CH$_2$Cl$_2$ (100 mL). The aqueous layer is extracted with CH$_2$Cl$_2$ (100 mL). The organic layer is removed in vacuo and insoluble material in the aqueous layer is filtered off. The resulting solid is recrystallized from ethanol to yield 0.825 g (83%) of the title compound as a white, crystalline solid.

Physical characteristics are as follows:

Mp 222–225° C.; $^1$H NMR (300 MHz, DMSO-d$_6$) δ 10.59, 8.70, 7.41–7.33, 7.30, 5.79, 4.72, 4.55, 3.96; $^{13}$C NMR (75 MHz, DMSO-d$_6$) δ 172.0, 164.4, 150.1, 145.2, 141.9, 138.6, 131.4, 130.7, 129.1, 128.3, 118.4, 114.3, 58.4, 42.9, 41.4; IR (drift) 3304, 2474, 1906, 1646, 1593, 1574, 1545, 1513, 1490, 1237, 1140, 1088, 1018, 800, 723 cm$^{-1}$; MS (ESI+) for m/z 363 (M+H)$^+$. Anal. Found: C, 56.15; H, 4.09; N, 7.60; Cl, 9.70; S, 8.81.

EXAMPLE 36

N-(4-Chlorobenzyl)-7-methyl-2-(4-morpholinylmethyl)-4-oxo-4,7-dihydrothieno[2,3-b]pyridine-5-carboxamide

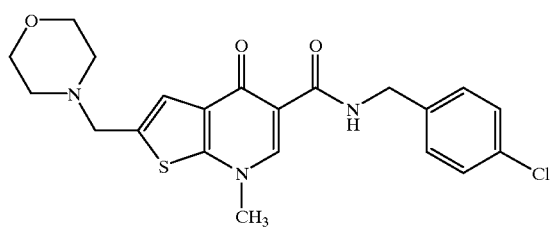

To a solution of N-(4-chlorobenzyl)-2-(hydroxymethyl)-7-methyl-4-oxo-4,7-dihydrothieno[2,3-b]pyridine-5-carboxamide (0.250 g) from Example No. 35 in DMF (14 mL) are added DMAP (13 mg), 2,4,6-collidine (0.23 mL), and methanesulfonyl chloride (0.13 mL). The reaction is stirred at rt for 1.5 h and then morpholine (0.60 mL, 6.9 mmol) is added. The reaction is stirred at rt for 18 h. The reaction mixture is poured into water (40 mL). The resulting off-white solid is filtered off and recrystallized from ethanol to yield 0.242 g (81%) of the title compound as an off-white, crystalline solid.

Physical characteristics are as follows:

Mp 230–236° C.; $^1$H NMR (300 MHz, DMSO-d$_6$) δ 10.59, 8.70, 7.41–7.32, 4.55, 3.96, 3.59, 2.45; $^{13}$C NMR (75 MHz, CDCl$_3$) δ 173.0, 165.0, 150.6, 144.5, 138.1, 137.4, 132.8, 131.6, 128.9, 128.7, 121.3, 115.8, 66.9, 57.7, 53.5, 43.1, 42.6; IR (drift) 2815, 1906, 1654, 1597, 1544, 1511, 1491, 1456, 1306, 1112, 865, 811, 806, 798, 729, cm$^{-1}$; MS (ESI+) for m/z 432 (M+H)$^+$. Anal. Found: C, 57.99; H, 5.20; N, 9.60; Cl, 8.23; S, 7.34.

EXAMPLE 37

N-(4-Chlorobenzyl)-7-methyl-2-(4-morpholinylmethyl)-4-oxo-4,7-dihydrothieno[2,3-b]pyridine-5-carboxamide Hydrochloride

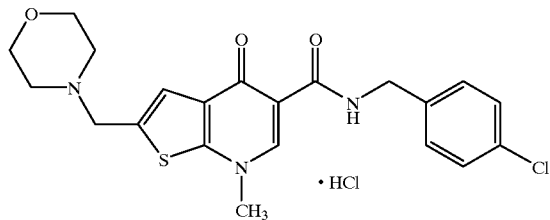

N-(4-chlorobenzyl)-7-methyl-2-(4-morpholinylmethyl)-4-oxo-4,7-dihydro-thieno[2,3-b]pyridine-5-carboxamide (1.50 g) from Example No. 36 is dissolved in methanolic HCl (50 mL) and concentrated in vacuo. The resulting off-white solid is recrystallized from methanol/ethanol to yield 1.458 g (90%) of the title compound as a white solid.

Physical characteristics are as follows:

Mp 27 8–280° C. (dec); $^1$H NMR (300 MHz, DMSO-d$_6$) δ 11.89, 10.47, 8.78, 7.76, 7.42–7.32, 4.66, 4.56, 4.05–3.90, 3.98, 3.85–3.73, 3.38–3.25, 3.18–3.02; $^{13}$C NMR (DMSO-d$_6$) δ 172.1, 164.0, 152.2, 146.1, 138.4, 131.3, 130.3, 129.0, 128.6, 128.2, 124.9, 114.5, 63.1, 52.6, 50.2, 42.9, 41.6; IR (drift) 2464, 2464, 2432, 2414, 2389, 2244, 1666, 1601, 1552, 1510, 1235, 1117, 1080, 804, 795 cm$^{-1}$; MS (ESI+) m/z 432 (M+H)$^+$; Anal. Found: C, 53.82; H, 4.97; N, 8.95; Cl, 15.16; S, 6.84.

EXAMPLE 38

N-(4-Chlorobenzyl)-7-methyl-4-oxo-2-(4-thiomorpholinyl-methyl)-4,7-dihydrothieno[2,3-b]pyridine-5-carboxamide

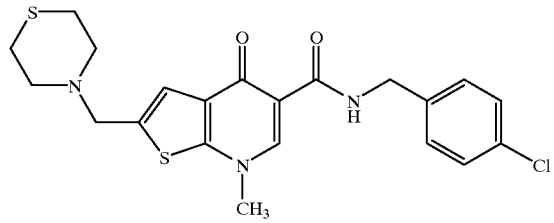

To a solution of N-(4-chlorobenzyl)-2-(hydroxymethyl)-7-methyl-4-oxo-4,7-dihydrothieno[2,3-b]pyridine-5-carboxamide (0.300 g) from Example No. 35 in DMF (16 mL) are added DMAP (16 mg), 2,4,6-collidine (0.27 mL), and methanesulfonyl chloride (0.16 mL). The reaction mixture is stirred at room temperature for 2 h and then thiomorpholine (0.83 mL) is added. The mixture is stirred at room temperature for 3 d and is then poured into water (50 mL). The resulting off-white solid is filtered off and recrystallized from ethanol to yield 0.222 g (60%) of the title compound as an off-white solid.

Physical characteristics are as follows:

Mp 215–218° C. (dec); $^1$H NMR (300 MHz, DMSO-d$_6$) δ 10.60, 8.70, 7.41–7.32, 4.55, 3.95, 2.74–2.72, 2.64–2.61; $^{13}$C NMR (CDCl$_3$) δ 180.6, 172.6, 158.1, 152.1, 146.4, 145.0, 140.4, 139.3, 136.6, 136.3, 128.7, 123.3, 65.7, 62.5, 50.7, 50.2, 35.6; IR (drift) 2814, 1654, 1597, 1545, 1511, 1491, 1456, 1375, 1340, 1306, 1285, 1240, 1139, 801, 722 cm$^{-1}$; HRMS (FAB) m/z 448.0915 (C$_{21}$H$_{22}$ClN$_3$O$_2$S$_2$+H); Anal. Found: C, 56.07; H, 5.03; N, 9.30; Cl, 7.79; S, 14.21.

EXAMPLE 39

N-(4-Chlorohenzyl)-2-(((2-hydroxy-2-(4-hydroxyphenyl)ethyl)(methyl)amino)methyl)-7-methyl-4-oxo-4,7-dihydrothieno[2,3-b]pyridine-5-carboxamide

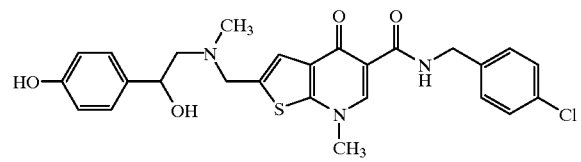

To a solution of N-(4-chlorobenzyl)-2-(hydroxymethyl)-7-methyl-4-oxo-4,7-dihydrothieno[2,3-b]pyridine-5-carboxamide (0.300 g) from Example No. 35 in DMF (17 mL) are added DMAP (16 mg), 2,4,6-collidine (0.27 mL), and methanesulfonyl chloride (0.16 mL). The reaction mixture is stirred at room temperature for 1 h and then syneph-rine (1.39 g) is added. The mixture is stirred at room temperature for 18 h and is then poured into water (50 mL). The resulting off-white solid is filtered off. Additional material precipitates out of the filtrate. The two lots of material are combined and purified by column chromatography (CH$_2$Cl$_2$, CH$_2$Cl$_2$/methanol, 99/1; 98/2; 96/4) to yield 0.253 g (60%) of the title compound as a white solid.

Physical characteristics are as follows:

Mp 187° C.; $^1$H NMR (300 MHz, DMSO-d$_6$) δ 10.61, 9.23, 8.69, 7.41–7.32, 7.29, 7.12, 6.70, 4.95, 4.66–4.61, 4.55, 3.92, 3.83, 2.65–2.47, 2.30; $^{13}$C NMR (DMSO-d$_6$) δ 171.8, 164.3, 156.1, 150.3, 145.0, 139.8, 138.5, 134.9, 131.2, 130.4, 129.0, 128.2, 127.2, 119.7, 114.5, 114.1, 70.2, 64.6, 56.2, 42.6, 42.3, 41.3; IR (drift) 1641, 1595, 1543, 1514, 1493, 1455, 1343, 1307, 1267, 1256, 1234, 1035, 1014, 839, 803 cm$^{-1}$; MS (ESI+) m/z 512 (M+H)$^+$; Anal. Found: C, 60.90; H, 5.12; N, 8.15; Cl, 6.99; S, 6.26.

EXAMPLE 40

N-(4-Chlorobenzyl)-2-(((2-hydroxy-2-phenylethyl)(methyl)-amino)methyl)-7-methyl-4-oxo-4,7-dihydrothieno[2,3-b]pyridine-5-carboxamide

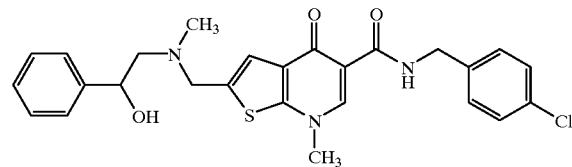

To solution of N-(4-chlorobenzyl)-2-(hydroxymethyl)-7-methyl-4-oxo-4,7-dihydrothieno[2,3-b]pyridine-5-carboxamide (0.300 g) from Example No. 35 in DMF (17 mL) are added DMAP (16 mg), 2,4,6-collidine (0.27 mL), and methanesulfonyl chloride (0.16 mL). The reaction mixture is stirred at room temperature for 1 h and then α-(methylaminomethyl)benzyl alcohol (1.26 g) is added. The mixture is stirred at room temperature for 18 h and is then poured into water (50 mL). The resulting off-white solid is filtered off and purified by column chromatography (CH$_2$Cl$_2$/methanol, 99/1; 97/3) to yield 0.261 g (63%) of the title compound as a pale yellow solid.

Physical characteristics are as follows:

Mp 184–187° C.; $^1$H NMR (300 MHz, DMSO-d$_6$) δ 10.61, 8.69, 7.41–7.21, 5.17, 4.79–4.73, 4.55, 3.92, 3.86, 2.69–2.50, 2.31; $^{13}$C NMR (DMSO-d$_6$) δ 171.8, 164.3, 150.3, 145.0, 144.6, 139.6, 138.5, 131.2, 130.4, 129.0, 128.2, 127.7, 126.7, 126.1, 119.9, 114.2, 70.5, 64.6, 56.2, 42.7, 42.2, 41.2; IR (drift) 1652, 1595, 1532, 1490, 1369, 1347, 1336, 1303, 1242, 1130, 1124, 1086, 803, 757, 697 cm$^{-1}$; MS (ESI+) m/z 496 (M+H)$^+$; Anal. Found: C, 63.01; H, 5.40; N, 8.29; Cl, 7.03; S, 6.37.

EXAMPLE 41

N-(4-Chlorobenzyl)-4-hydroxy-2-(4-morpholinylmethyl)-thieno[2,3-b]pyridine-5-carboxamide

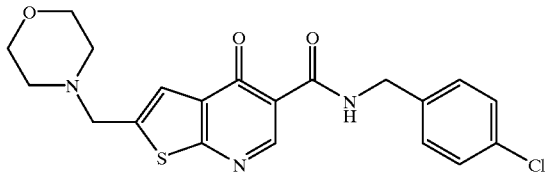

Formaldehyde (2.6 mL) is added to morpholine (2.7 mL) at 0° C. Ethanol (10 mL) is then added followed by addition of N-(4-chlorobenzyl)-4-hydroxythieno[2,3-b]pyridine-5-carboxamide (1.00 g) from Example No. 1. Acetic acid (2 mL) is added, and the reaction mixture is allowed to warm to rt and then refluxed for 18 h. Additional morpholine (2.7 mL) and formaldehyde (2.6 mL) are added and the reaction is refluxed for an additional 24 h. The reaction mixture is allowed to cool to room temperature and is then concentrated in vacuo. The residue is treated with 25% NaOH (20 mL). The aqueous layer is extracted with ethyl acetate (50 mL) then CHCl$_3$ (60 mL). Methanol (30 mL) is added to the aqueous layer and it is extracted with CHCl$_3$ (2×60 mL). This procedure is repeated 3 times. The combined organic layers are dried with MgSO$_4$, filtered, and concentrated in vacuo. The resulting brown solid is purified by column chromatography (CH$_2$Cl$_2$/methanol, 98/2; 96/4) to yield a tan solid which is recrystallized from ethyl acetate/Et$_2$O to yield 0.718 g (55%) of the title compound as an off-white solid.

Physical characteristics are as follows:

Mp 193–195° C.; $^1$H NMR (300 MHz, DMSO-d$_6$) δ 13.30, 10.59, 8.66, 7.41–7.33, 7.27, 4.54, 3.72, 3.58, 2.44; IR (drift) 2958, 2926, 2912, 2853, 2845, 2810, 1641, 1595, 1550, 1492, 1118, 866, 800, 791, 785 cm$^{-1}$; MS (FAB) m/z 418 (MH$^+$, 99), 420 (42), 419 (33), 418 (99), 417 (19), 416 (17), 331 (17), 125 (21), 100 (22); HRMS (FAB) m/z 418.0996 (C$_{20}$H$_{20}$ClN$_3$O$_3$S+H); Anal. Found: C, 57.07; H, 5.02; N, 9.94; Cl, 8.45; S, 7.51.

EXAMPLE 42

N-(4-Chlorobenzyl)-7-ethyl-2-(4-morpholinylmethyl)-4-oxo-4,7-dihydrothieno[2,3-b]pyridine-5-carboxamide

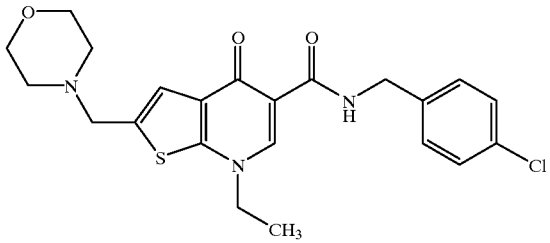

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added iodoethane (88 µL). The reaction mixture is allowed to stir at room temperature for 24 h. The resulting suspension is poured into water (25 mL), filtered, and washed with water (5 mL) followed by diethyl ether (5 mL). The resulting crude solid is purified by recrystallization from ethanol to afford 325 mg (73%) of the title compound as a white solid.

Physical characteristics are as follows:

Mp 194–196° C.; $^1$H NMR (300 MHz, DMSO-d$_6$) δ 10.59, 8.73, 7.41–7.32, 4.54, 4.32, 3.75, 3.59, 2.46, 1.44; $^{13}$C NMR (75 MHz, DMSO-d$_6$) δ 171.9, 164.3, 149.3, 143.9, 138.6, 138.0, 131.4, 131.1, 129.1, 128.4, 120.6, 114.7, 66.2, 56.6, 53.0, 51.5, 41.4, 14.0; IR (drift) 2813, 1653, 1597, 1563, 1543, 1507, 1455, 1349, 1328, 1302, 1226, 1116, 867, 803, 795 cm$^{-1}$; MS (ESI+) m/z 446 (100, (M+H)$^+$), 447 (30), 448 (40); HRMS (FAB) m/z 446.1304 (C$_{22}$H$_{24}$ClN$_3$O$_3$S+H). Anal. Found (C$_{22}$H$_{24}$ClN$_3$O$_3$S): C, 59.16; H, 5.45; N, 9.40; Cl, 7.99; S, 7.21.

EXAMPLE 43

N-(4-Chlorobenzyl)-2-(4-morpholinylmethyl)-4-oxo-7-propyl-4,7dihydrothieno[2,3-b]pyridine-5-carboxamide

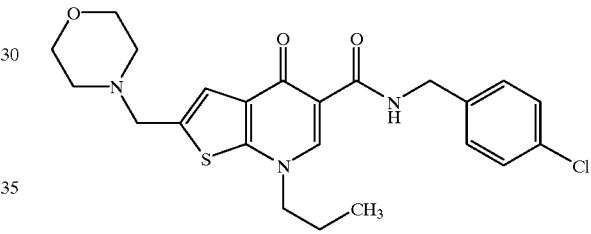

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added 1-iodopropane (107 µL). The reaction mixture is allowed to stir at room temperature for 4 h. Additional 1-iodopropane (107 µL) is added and the mixture is heated to 60° C. for 2 h. The mixture is allowed to cool to room temperature and stand for 18 h. The resulting suspension is poured into water (25 mL), filtered, and washed with water (5 mL) followed by diethyl ether (5 mL). The resulting crude solid is purified by recrystallization from ethanol to afford 335 mg (73%) of the title compound as a white solid.

Physical characteristics are as follows:

Mp 174–176° C.; $^1$H NMR (300 MHz, DMSO-d$_6$) δ 10.58, 8.71, 7.42–7.33, 4.54, 4.26, 3.74, 3.59, 2.45, 1.86, 0.90; $^{13}$C NMR (75 MHz, DMSO-d$_6$) δ 171.9, 164.3, 149.6, 144.4, 138.6, 137.9, 131.4, 131.1, 129.1, 128.3, 120.6, 114.4, 66.1, 57.6, 56.6, 52.9, 41.4, 21.6, 10.6; IR (drift) 2968, 1652, 1593, 1540, 1505, 1458, 1351, 1343, 1327, 1300, 1226, 1111, 1014, 865, 808 cm$^{-1}$; MS (ESI+) m/z 460 (100, (M+H)$^+$), 461 (28), 462 (40); HRMS (FAB) m/z 460.1461 (C$_{23}$H$_{26}$ClN$_3$O$_3$S+H). Anal. Found (C$_{23}$H$_{26}$ClN$_3$O$_3$S): C, 60.03; H, 5.76; N, 9.11; Cl, 7.75; S, 6.95.

EXAMPLE 44

N-(4-Chlorobenzyl)-7-isopropyl-2-(4-morpholinylmethyl)-4-oxo-4,7-dihydrothieno[2,3-b]pyridine-5-carboxamide

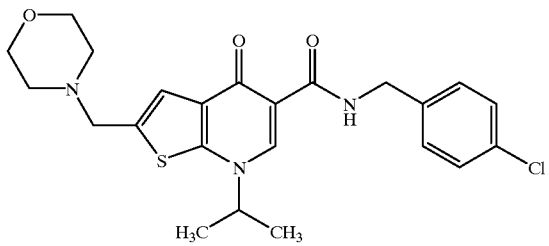

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added 2-bromopropane (103 μL). The reaction mixture is stirred at room temperature for 4 h. Additional 2-bromopropane (103 μL) is added and the mixture is heated to 60° C. for 20 h. The reaction mixture is allowed to cool to room temperature, is poured into water (25 mL), and then extracted with EtOAc (3×25 mL). The organic layer is dried (Na$_2$SO$_4$) and concentrated. The resulting crude solid is purified by recrystallization from ethanol to afford 173 mg (38%) of the title compound as a white solid.

Physical characteristics are as follows:

Mp 191–195° C.; $^1$H NMR (300 MHz, DMSO-d$_6$) δ 10.59, 8.67, 7.41–7.33, 4.60–4.53, 3.75, 3.59, 2.46, 1.55; $^{13}$C NMR (75 MHz, DMSO-d$_6$) δ 171.8, 164.3, 149.5, 139.6, 138.6, 137.8, 131.7, 131.2, 129.2, 128.3, 120.7, 114.8, 66.2, 58.3, 56.6, 53.0, 41.4, 21.1; IR (drift) 2968, 1662, 1593, 1541, 1503, 1409, 1342, 1331, 1295, 1218, 1144, 1112, 1014, 867, 800 cm$^{-1}$; MS (ESI+) m/z 460 (100, (M+H)$^+$), 461 (30), 462 (40); HRMS (FAB) m/z 460.1463 (C$_{23}$H$_{26}$ClN$_3$O$_3$S+H). Anal. Found (C$_{23}$H$_{26}$ClN$_3$O$_3$S): C, 59.92; H, 5.71; N, 9.08; Cl, 7.74; S, 7.01.

PREPARATION 1

N-(3-tert-Butoxycarbonyl-thien-2-yl)-aminomethylene-malonic Acid Diethyl Ester

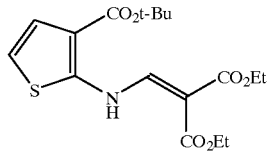

The title compound was prepared from tert-butyl 2-aminothiophene-3-carboxylate as described in German patent 2447477 (1976). A solution of tert-butyl 2-aminothiophene-3-carboxylate (14.0 g, obtained through a slight modification of procedures employed by M. Gutschow and U. Neumann, J. Med. Chem. 1998, 41, 1729–1740) and diethyl ethoxymethylene malonate (14.2 ml) in toluene (50 ml) is heated to about 100° C. for about 24 hr. The solution is cooled slowly to about −20° C. and filtered. The crystals are washed with cold toluene and dried in a vacuum oven at 30° C. to afford a 79.5% yield of the title compound as pale yellow crystals.

Physical characteristics are as follows:

$^1$H NMR (400 MHz, CDCl$_3$) δ 8.2, 7.1, 6.6, 4.35, 4.25, 1.55, 1.39); $^{13}$C NMR (100 MHz, CDCl$_3$) δ 166.63, 165.48, 163.36, 152.46, 149.86, 127.69, 115.98, 112.79, 97.22, 81.97, 60.76, 60.52, 28.37, 14.34, 14.32.

PREPARATION 2

N-(3-tert-Butoxycarbonyl-thien-2-yl)-methylaminomethylenemalonic Acid Diethyl Ester

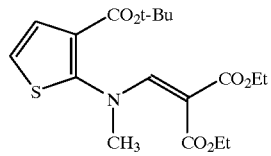

Iodomethane (3.0 ml) is added to a mixture of N-(3-tert-butoxycarbonyl-thien-2-yl)-aminomethylenemalonic acid diethyl ester (15.0 g) from Preparation No. 1 and anhydrous potassium carbonate (8.4 g) in DMF (67 ml). The mixture is stirred vigorously at ambient temperature for about 20 hr. Water (150 ml) is added and the solution is extracted with toluene (2×75 ml). The combined toluene layers are washed with water (2×150 ml) and the solvent is removed in vacuo to provide 15.8 g of the title compound as a dark yellow oil.

Physical characteristics are as follows:

$^1$H NMR (300 MHz, CDCl$_3$) δ 7.5, 7.3, 7.2, 4.2, 3.96, 3.36, 1.55, 1.25; $^{13}$C NMR (75 MHz, CDCl$_3$) δ 166.31, 160.57, 149.37, 128.14, 127.98, 121.42, 99.45, 81.85, 60.87, 60.21, 28.08, 14.27, 13.86.

PREPARATION 3

N-(3-tert-Butoxycarbonyl-5-morpholinomethyl-thien-2-yl)-methylaminomethylenemalonic Acid Diethyl Ester

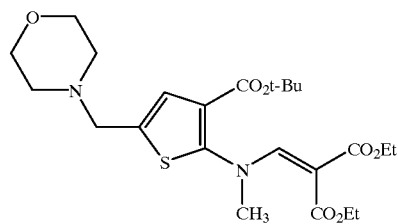

A mixture of N-(3-tert-butoxycarbonyl-thien-2-yl)-methylaminomethylene-malonic acid diethyl ester (19.0 g) from Preparation No. 2 and 4-methylene morpholinium chloride (Dimmock, JR, et al Eur. J. Med. Chem. 1989, 24, 379–383) (13.4 g) in dry acetonitrile (50 ml) is heated at reflux for about 4 hr. The solution is then cooled in an ice bath and saturated aqueous sodium carbonate (98 ml) is slowly added. The solution is extracted three times with ethyl acetate (300 ml total) and the combined organic layers are then washed three times with water (600 ml total). The solvents are removed in vacuo to afford 23.0 g (96%) of the title compound as a brown oil.

Physical characteristics are as follows:

$^1$H NMR (400 MHz, CDCl$_3$) δ 7.45, 7.06, 4.1, 3.70, 3.60, 3.34, 2.50, 1.54, and 1.2; $^{13}$C NMR (100 MHz, CDCl$_3$) δ 166.44, 160.71, 149.45, 125.73, 99.35, 81.86, 66.95, 60.85, 60.27, 57.79, 53.35, 28.16, 14.36, 13.98.

PREPARATION 4

Ethyl 7-Methyl-2-(4-morpholinomethyl)-4-oxo-4,7-dihydrothieno[2,3-b]pyridine-5-carboxylate

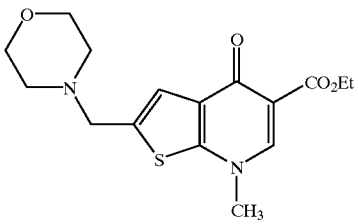

Phosphorus pentoxide (1.20 g) is dissolved in anhydrous methanesulfonic acid (7.2 ml) with warming to 50° C. as needed. The solution is cooled to room temperature and a solution of N-(3-tert-butoxycarbonyl-5-morpholinomethyl-thien-2-yl)-methylaminomethylenemalonic acid diethyl ester (2.00 g) from Preparation No. 3 in toluene (2 ml) is added with vigorous stirring. After about 30 min at ambient temperature the two phase system is warmed to 35° C. and maintained for about 2 hr. With ice bath cooling, saturated aqueous sodium carbonate (64 ml) is added very slowly with vigorous stirring. The mixture is extracted twice with methylene chloride (80 ml total). The solvent is removed in vacuo to give 1.10 g of tan crystals. The solid is recrystallized from ethyl acetate (16 ml) on the steam bath, and the solution is slowly cooled to 0–5° C. overnight. The resulting pale tan crystals are filtered and washed with cold ethyl acetate. The product is dried in a vacuum oven at 30° C. overnight to provided 0.58 g (42%) of the title compound.

Physical characteristics are as follows:
$^1$H NMR (300 MHz, CDCl$_3$) δ 8.24, 7.41, 4.36, 3.83, 3.72, 2.52, 1.39; $^{13}$C NMR (75 MHz, CDCl$_3$) δ 170.71, 165.53, 149.69, 145.61, 136.96, 132.77, 122.18, 115.17, 66.85, 60.83, 57.63, 53.37, 42.70, 14.31.

PREPARATION 5

7-Methyl-2-(4-morpholinomethyl)-4-oxo-4,7-dihydrothieno[2,3-b]pyridine-5-carboxylic Acid

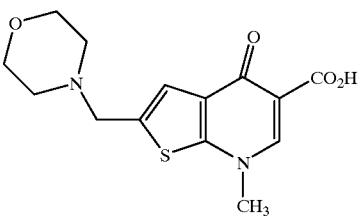

A mixture of ethyl 7-methyl-2-(4-morpholinomethyl)-4-oxo-4,7-idihydrothieno[2,3-b]pyridine-5-carboxylate (0.50 g) from Preparation No. 4, ethanol (2.5 ml), water (2.5 ml) and 50% sodium hydroxide (0.56 ml) is refluxed for 30 min. The ethanol is removed by distillation in vacuo. The residue is extracted with methyl t-butyl ether and then the pH is lowered to about 4 with 6 M HCl. The mixture is cooled to about 0° C. and filtered cold rinsing with cold water. The light brown solid is dried in a vacuum oven at 40° C. for two days to afford 0.45 g (98%) of the title compound.

Physical characteristics are as follows:
$^1$H NMR (400 MHz, D$_2$O) δ 8.6, 7.68, 4.66, 4.00, 3.92, 3.38; $^{13}$C NMR (100MHz, D$_2$O) δ 174.00, 169.02, 155.00, 147.70, 129.53, 128.02, 127.41, 111.20, 64.17, 54.47, 51.75, 44.53.

PREPARATION 6

N-(4-Chlorobenzyl)-7-methyl-2-(4-morpholinylmethyl)-4-oxo-4,7-dihydrothieno[2,3-b]pyridine-5-carboxamide

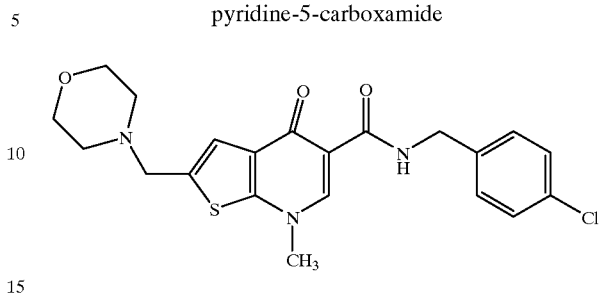

7-Methyl-2-(4-morpholinomethyl)-4-oxo-4,7-dihydrothieno[2,3-b]pyfidine-5-carboxylic acid (1.09 g) from Preparation No. 5 and 1,1'-carbonyldiimidazole (0.86 g) are dissolved in dry N,N-dimethylformamide (9.8 ml) and heated to 65–70° C. for 3.5 hr. To the reaction mixture is added 4-chlorobenzylamine (0.44 ml) and the mixture is heated for about 1.5 hr at 65–70° C. The reaction mixture is diluted with water (6.5 ml) and cooled to about 0° C. The crude product is filtered cold, washed with cold water, and is dried at about 45° C. in a vacuum oven overnight to afford 1.29 g (85%) of the title compound.

Physical characteristics are as follows:
$^1$H NMR (300 MHz, CDCl$_3$) δ 10.61, 8.59, 7.41, 7.28, 4.61, 3.88, 3.72, 2.53.

EXAMPLE 45

N-(4-Fluorobenzyl)-7-methyl-2-(4-morpholinylmethyl)-4-oxo-4,7-dihydrothieno[2,3-b]pyridine-5-carboxamide

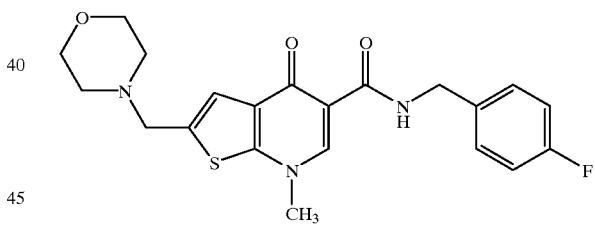

A mixture of ethyl 7-methyl-2-(4-morpholinylmethyl)-4-oxo-4,7-dihydro-thieno[2,3-b]pyridine-5-carboxylate (0.300 g) from Preparation No. 4 and 4-fluorobenzylamine (1.02 mL) is stirred at 175° C. for 3 h. The reaction mixture is allowed to cool for several minutes and is then diluted with toluene (15 mL). The resulting off-white precipitate is filtered off and recrystallized from acetonitrile then ethanol to yield 0.184 g (50%) of the title compound as a white, crystalline solid.

Physical characteristics are as follows:
Mp 214–216° C.; $^1$H NMR (300 MHz, DMSO-d$_6$) δ 10.57, 8.71, 7.39–7.34, 7.19–7.13, 4.54, 3.96, 3.75, 3.59, 2.45; $^{13}$C NMR (CDCl$_3$) δ 173.0, 164.9, 163.6, 160.3, 150.6, 144.5, 138.1, 134.6, 134.5, 131.6, 129.3, 121.3, 115.7, 115.5, 115.2, 66.9, 57.7, 53.4, 43.0, 42.5; IR (drift) 2810, 1662, 1597, 1541, 1509, 1370, 1342, 1332, 1303, 1218, 1149, 1113, 820, 804, 797 cm$^{-1}$; MS (ESI+) m/z 416 (M+H)$^+$; Anal. Found: C, 60.57; H, 5.43; N, 10.02; S, 7.49; F, 4.68.

EXAMPLE 46

N-(4-Bromobenzyl)-7-methyl-2-(4-morpholinylmethyl)-4-oxo-4,7-dihydrothieno[2,3-b]pyridine-5-carboxamide

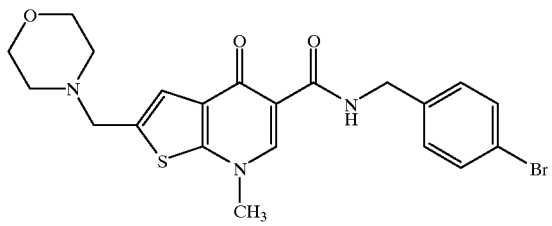

4-Bromobenzylamine (1.98 g) is suspended in CH$_2$Cl$_2$ (50 mL) and stirred with a 10% aqueous NaOH solution (25 mL). The organic layer is removed and the aqueous layer is extracted with CH$_2$Cl$_2$ (2×25 mL). The combined organic layers are dried (MgSO$_4$), filtered, and concentrated in vacuo. Ethyl 7-methyl-2-(4-morpholinylmethyl)-4-oxo-4,7-dihydrothieno[2,3-b]pyridine-5-carboxylate from Preparation No. 4 (0.300 g) is then added to the free amine, and the mixture is stirred at 190° C. for 1 h. The reaction mixture is allowed to cool for several minutes and is then diluted with toluene (10 mL). The resulting pale yellow precipitate is filtered off and recrystallized from ethanol to yield 0.272 g (64%) of the title compound as a white solid.

Physical characteristics are as follows:

Mp 245–246° C.; $^1$H NMR (300 MHz, DMSO-d$_6$) δ 10.60, 8.70, 7.54, 7.35, 7.29, 4.53, 3.96, 3.75, 3.59, 2.45; $^{13}$C NMR (CDCl$_3$) δ 173.0, 165.0, 144.6, 137.9, 131.6, 129.3, 120.9, 115.7, 66.8, 57.6, 53.4, 43.1, 42.6; IR (drift) 2815, 1653, 1597, 1542, 1511, 1486, 1372, 1306, 1118, 1112, 1010, 865, 805, 798, 729 cm$^{-1}$; MS (ESI+) m/z 476 (M+H)$^+$. Anal. Found: C, 52.64; H, 4.66; N, 8.76; Br, 16.56; S, 6.65.

EXAMPLE 47

N-(4-Chlorobenzyl)-4-hydroxy-2-(4-morpholinylcarbonyl)-thieno[2,3-b]pyridine-5-carboxamide

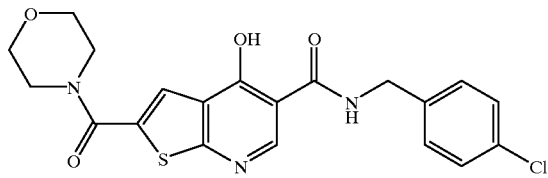

To a solution of N-(4-chlorobenzyl)-4-hydroxy-2-iodothieno[2,3-b]pyridine-5-carboxamide (2.00 g) from Example No. 2 in DMF (45 mL) are added triethylamine (1.25 mL), morpholine (15.7 mL), Pd(OAc)$_2$ (0.101 g), and dppp (0.186 g). The reaction mixture is degassed by bubbling N$_2$ through the solution for 15 minutes. Carbon monoxide is then bubbled through the solution, and the reaction mixture is heated to 70° C. and stirred for 18 h. The reaction mixture is allowed to cool to room temperature and water (25 mL) and 2 N HCl (75 mL) are added. The resulting green solid is filtered off and the filtrate is extracted with CH$_2$Cl$_2$ (4×100 mL). The combined organic layers are dried with MgSO$_4$, filtered, and concentrated in vacuo. The resulting orange oil is purified by column chromatography (CH$_2$Cl$_2$; CH$_2$Cl$_2$/methanol, 98/2). The resulting pale yellow solid is recrystallized from acetonitrile to yield 0.648 g (33%) of the title compound as an off-white solid.

Physical characteristics are as follows:

Mp 217–219° C.; $^1$H NMR (300 MHz, CDCl$_3$) δ 8.72, 7.67, 7.31–7.25, 4.68, 3.86, 3.80; $^{13}$C NMR (CDCl$_3$) δ 165.8, 162.3, 142.1, 136.3, 133.2, 131.7, 128.8, 128.7, 123.7, 66.7, 43.0; IR (drift) 2923, 2854, 2769, 2760, 1662, 1603, 1569, 1541, 1509, 1488, 1458, 1432, 1274, 1113, 791, cm$^{-1}$; MS (ESI–) m/z 430 (M–H)$^-$. Anal. Found: C, 55.47; H, 4.16; N, 9.76; Cl, 8.29; S, 7.50.

EXAMPLE 48

N-(4-Chlorobenzyl)-7-methyl-2-(4-morpholinylcarbonyl)-4 dothieno[2,3-b]pyridine-5-carboxamide

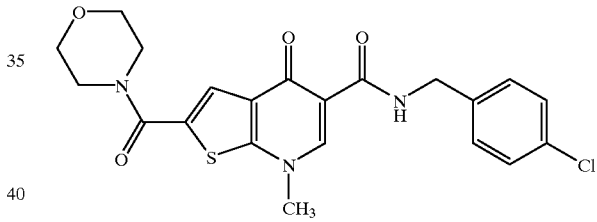

To a solution of N-(4-chlorobenzyl)-4-hydroxy-2-(4-morpholinyicarbonyl)-thieno[2,3-b]pyridine-5-carboxamide (0.527 g) from Example No. 47 in DMF (10 mL) is added potassium carbonate (0.337 g) followed by iodomethane (0.11 mL). The reaction mixture is stirred at room temperature for 1 h. The reaction mixture is then poured into water (25 mL). The resulting off-white solid is filtered off and recrystallized from acetonitrile to yield 0.448 g (82%) of the title compound as a white solid.

Physical characteristics are as follows:

Mp 244–245° C. (dec); $^1$H NMR (300 MHz, CDCl$_3$) δ 10.37, 8.66, 7.81, 7.34–7.28, 4.65, 3.94, 3.85, 3.77; $^{13}$C NMR (CDCl$_3$) δ 173.6, 164.4, 161.7, 152.0, 145.9, 137.1, 133.0, 132.4, 131.1, 129.0, 128.7, 124.5, 116.3, 66.7, 43.2, 42.7; IR (drift) 1655, 1607, 1550, 1525, 1488, 1451, 1428, 1303, 1273, 1253, 1133, 1114, 999, 802, 731 cm$^{-1}$; MS (ESI+) m/z 446 (M+H)$^+$; Anal. Found: C, 56.50; H, 4.52; N, 9.47; Cl, 7.96; S, 7.23. HRMS (FAB) m/z 466.1416 (C$_{22}$H$_{22}$F$_3$N$_3$O$_3$S+H). Anal. Found: C, 56.70; H, 4.83; N, 9.02; S, 6.70; F, 12.89.

EXAMPLE 49

7-Benzyl-N-(4-chlorobenzyl)-2-(4-morpholinylmethyl)-4-oxo-4,7-dihydrothieno[2,3-b]pyridine-5-carboxamide

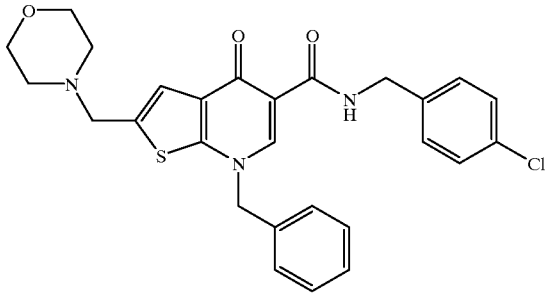

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added benzylbromide (130 μL). The reaction mixture is allowed to stir at room temperature for 18 h. The resulting suspension is poured into water (10 mL), filtered, and washed with water (5 mL) followed by diethyl ether (5 mL). The resulting crude solid is purified by recrystallization from ethanol to afford 400 mg (79%) of the title compound as a white solid.

Physical characteristics are as follows:

Mp 225–226.5° C.; $^1$H NMR (300 MHz, DMSO-$d_6$) δ 10.56, 8.92, 7.43–7.32, 5.58, 4.54, 3.68, 3.55, 2.39; $^{13}$C NMR (75 MHz, DMSO-$d_6$) δ 172.0, 164.2, 149.7, 145.0, 138.5, 138.3, 134.2, 131.4, 131.3, 129.2, 129.0, 128.5, 128.3, 127.6, 120.4, 114.6, 66.1, 58.9, 56.5, 52.9, 41.4; IR (drift) 1646, 1592, 1541, 1498, 1454, 1342, 1327, 1297, 1219, 1119, 1112, 868, 806, 740, 699 cm$^{-1}$; MS (ESI+) m/z 508 (100, (M+H)$^+$), 509 (30), 510 (40). Anal. Found ($C_{27}H_{26}ClN_3O_3S$): C, 63.71; H, 5.22; 8.25; Cl, 7.13; S, 6.40.

EXAMPLE 50

N-(4-Chlorobenzyl)-7-(3-fluorobenzyl)-2-(4-morpholinyl-methyl)-4-oxof47-dihydrothieno[2,3-b]pyridine-5-carboxamide

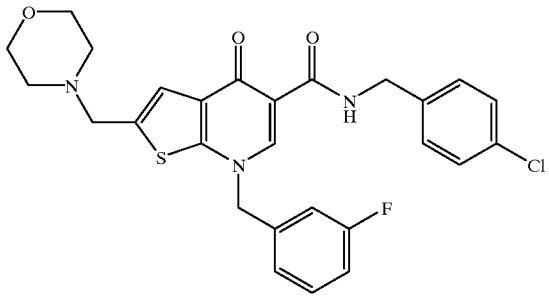

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added 3-fluoro-benzylbromide (135 μL). The reaction mixture is allowed to stir at room temperature for 18 h. The resulting suspension is poured into water (10 mL), filtered, and washed with water (5 mL) followed by diethyl ether (5 mL). The resulting crude solid is purified by recrystallization from ethanol to afford 425 mg (81%) of the title compound as a white solid.

Physical characteristics are as follows:

Mp 214–215° C.; $^1$H NMR (300 MHz, DMSO-$d_6$) δ 10.55, 8.93, 7.48–7.12, 5.60, 4.55, 3.69, 3.55, 2.39; $^{13}$C NMR (75 MHz, DMSO-$d_6$) δ 172.1, 164.2, 162.2 (d, J=245 Hz), 149.6, 145.1, 138.4, 137.0, 131.4, 131.1, 129.2, 128.3, 123.6, 120.5, 115.5, 115.3, 114.8, 114.7, 114.5, 66.1, 58.2, 56.5, 52.9, 41.4; IR (drift) 1649, 1593, 1543, 1502, 1492, 1453, 1327, 1299, 1266, 1258, 1213, 1118, 1112, 808, 788 cm$^{-1}$; MS (ESI+) m/z 526 (100, (M+H)$^+$), 527 (30), 528 (40). Anal. Found ($C_{27}H_{25}ClFN_3O_3S$): C, 61.42; H, 4.81; N, 7.95; Cl, 6.70; S, 6.09.

EXAMPLE 51

N-(4-Chlorobenzyl)-2-(4-morpholinylmethyl)-4-oxo-7-(3-phenylpropyl)-4,7-dihydrothieno[2,3-b]pyridine-5-carboxamide

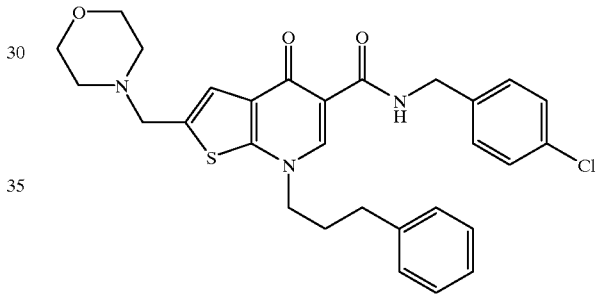

N-(4-Chlorobenzyl)Ahydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added 1-bromo-3-phenylpropane (167 μL). The reaction mixture is allowed to stir at room temperature for 72 h. The reaction mixture is poured into water (25 mL) and extracted with EtOAc (2×25 mL). The organic layer is dried (Na$_2$SO$_4$) and concentrated. The resulting crude solid is purified by recrystallization from ethanol to afford 277 mg (52%) of the title compound as a white solid.

Physical characteristics are as follows:

Mp 169–171° C.; $^1$H NMR (300 MHz, DMSO-$d_6$) δ 10.57, 8.70, 7.41–7.16, 4.54, 4.30, 3.73, 3.59, 2.67, 2.45, 2.17; $^{13}$C NMR (75 MHz, DMSO-$d_6$) δ 171.9, 164.3, 149.6, 144.2, 140.5, 138.6, 137.9, 131.4, 131.1, 129.1, 128.4, 128.3, 128.2, 126.0, 120.5, 114.5, 66.2, 56.6, 55.9, 52.9, 41.4, 31.7, 29.7; IR (drift) 1665, 1595, 1539, 1505, 1330, 1301, 1221, 1117, 1111, 868, 808, 799, 750, 719, 703 cm$^{-1}$; MS (ESI+) m/z 536 (100, (M+H)$^+$), 537 (30), 538 (40). Anal. Found ($C_{29}H_{30}ClN_3S$): C, 64.74; H, 5.66; N, 7.80; Cl, 6.54; S, 5.93.

EXAMPLE 52

N-(4-Chlorobenzyl)-2-(4-morpholinylmethyl)-4-oxo-7-tetahyro-2-furanylmethyl)-4,7-dihydrothieno[2,3-b]pyridine-5-carboxamide

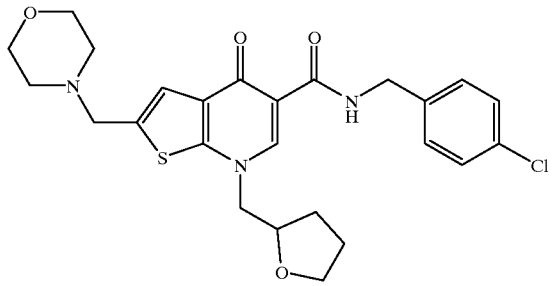

N-(4-Chlorobenzyl)-4-hydroxy-2-(4-morpholinylmethyl)thieno[2,3-b]pyridine-5-carboxamide (418 mg) from Example No. 41 and potassium carbonate (152 mg) are suspended in DMF (10 mL) and to the mixture is added tetrahydrofurfurylbromide (125 μL). The reaction mixture is heated to 60° C. for 4 h and then allowed to stand at room temperature for 18 h. The reaction mixture is poured into water (25 mL) and extracted with EtOAc (3×25 mL). The organic layer is dried ($Na_2SO_4$) and concentrated. The resulting crude solid is purified by recrystallization from ethanol to afford 15 mg (3%) of the title compound as a white solid.

Physical characteristics are as follows:

Mp 191–195° C.; $^1$H NMR (300 MHz, DMSO-$d_6$) δ 10.57, 8.67, 7.42–7.33, 4.54, 4.41–4.2, 3.83–3.72, 3.75, 3.70–3.60, 3.59, 2.07, 2.10–1.92, 1.90–1.75, 1.68–1.52; MS (ESI+) m/z 502 (100, (M+H)$^+$), 503 (30), 504 (40). Anal. Found ($C_{25}H_{28}ClN_3O_4S$): C, 59.46; H, 5.73; N, 8.19.

EXAMPLE 53

N-(4-Chlorobenzyl)-2-(4-morpholinylmethyl)-4-oxo-7-[2-(1-pyrrolidinyl)ethyl]-4,7-dihydrothieno[2,3-b]pyridine-5-carboxamide

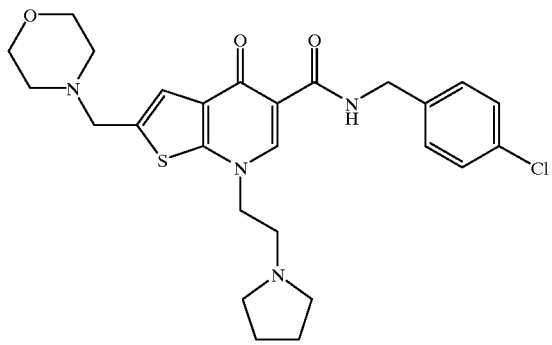

1,4-Diethylazodicarboxylate (205 μL) is added to a solution of N-(4-chlorobenzyl)-4-hydroxy-2-(4-morpholinylmethyl)thieno[2,3-b]pyridine-5-carboxamide (418 mg) from Example No. 41, triphenylphospine (341 mg), and 1-(2-hydroxyethyl)pyrrolidine (292 μL) in THF (10 mL). The reaction mixture is stirred at room temperature for 20 h and then poured into 0.5 N aqueous NaOH solution (25 mL). The mixture is extracted with EtOAc (3×25 mL). The organic layer is dried ($Na_2SO_4$) and concentrated. The crude product is purified by column chromatography ($CH_2Cl_2$/methanol, 100/1; 50/1; 20/1; 10/1) followed by recrystallization from ethanol to afford 54 mg (11%) of the title compound as a white solid.

Physical characteristics are as follows:

Mp 178–180° C.; $^1$H NMR (300 MHz, DMSO-$d_6$) δ 10.57, 8.69, 7.42–7.33, 4.53, 4.38, 3.75, 3.59, 2.89, 2.51–2.45, 1.69–1.62; IR (drift) 1651, 1592, 1559, 1532, 1502, 1457, 1327, 1296, 1143, 1119, 1110, 868, 811, 806, 800 cm1; MS (ESI+) m/z 515 (100, (M+H)$^+$), 516 (30), 517 (40). Anal. Found ($C_{26}H_{31}ClN_4O_3S$): C, 60.48; H, 6.04; N, 10.72; Cl, 6.99; S, 6.25.

EXAMPLE 54

N-(4-Chlorobenzyl)-2-(4-morpholinylmethyl)-4-oxo-7-(3-pyridinylmethyl)-4,7-dihydrothieno[2,3-b]pyridine-5-carboxamide

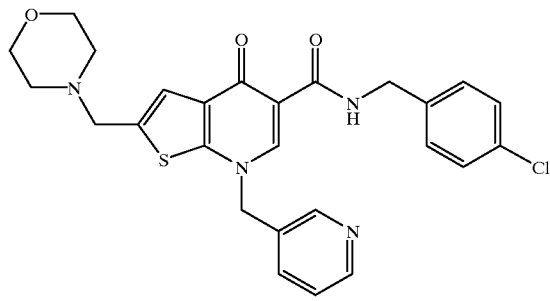

1,4-Diethylazodicarboxylate (205 μL) is added to a solution of N-(4-chlorobenzyl)-4-hydroxy-2-(4-morpholinylmethyl)thieno[2,3-b]pyridine-5-carboxamide (418 mg) from Example No. 41, triphenylphospine (341 mg), and 3-pyridylmethanol (243 μL) in THF (10 mL). The reaction mixture is stirred at room temperature for 20 h and then the resulting suspension is filtered. The crude product is purified by recrystallization from ethanol to afford 63 mg (12%) of the title compound as a white solid.

Physical characteristics are as follows:

Mp 214–215° C.; $^1$H NMR (300 MHz, DMSO-$d_6$) δ 10.54, 8.97, 8.65, 8.57, 7.73, 7.44–7.33, 5.64, 4.55, 3.69, 3.55, 2.40; IR (drift) 1646, 1592, 1542, 1501, 1420, 1341, 1325, 1297, 1267, 1209, 1111, 865, 807, 794, 716 cm$^{-1}$; MS (ESI+) for m/z 509 (100, (M+H)$^+$), 510 (30), 511 (40). Anal. Found ($C_{26}H_{25}ClN_4O_3S$): C, 61.20; H, 4.98; N, 10.92; Cl, 6.94; S, 6.26.

EXAMPLE 55

N-(4-Chlorobenzyl)-2-(4-morpholinylmethyl)-4-oxo-7-(4-pyridinylmethyl)-4,7-dihydrothieno[2,3-b]pyridine-5-carboxamide

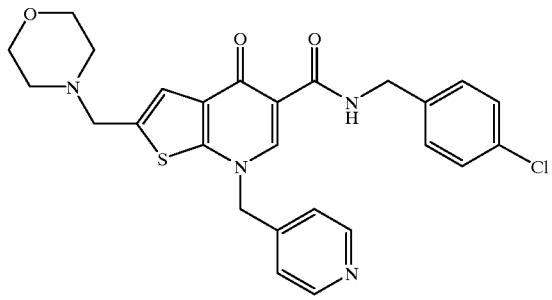

1,4-Diethylazodicarboxylate (205 μL) is added to a solution of N-(4-chlorobenzyl)-4-hydroxy-2-(4-morpholinylmethyl)thieno[2,3-b]pyridine-5-carboxamide (418 mg) from Example No. 41, triphenylphospine (341 mg), and 4-pyridylmethanol (273 mg) in THF (10 mL). The reaction mixture is stirred at room temperature for 20 h and then poured into 0.5 N aqueous NaOH solution (25 mL). The mixture is extracted with EtOAc (3×25 mL). The organic layer is dried ($Na_2SO_4$) and concentrated. The crude product is purified by column chromatography ($CH_2Cl_2$/methanol, 50/1; 20/1) followed by recrystallization from ethanol to afford 107 mg (21%) of the title compound as a white solid.

Physical characteristics are as follows:

Mp 208–210° C. (dec); $^1$H NMR (300 MHz, DMSO-$d_6$) δ 10.55, 8.95, 8.56, 7.43–7.35, 7.34, 7.25, 5.67, 4.56, 3.68, 3.54, 2.39; IR (drift) 2812, 1648, 1593, 1550, 1543, 1500, 1416, 1345, 1328, 1299, 1117, 1111, 866, 805, 795 $cm^{-1}$; MS (ESI+) for m/z 509 (100, $(M+H)^+$), 510 (30), 511 (40); HRMS (FAB) m/z 509.1424 ($C_{26}H_{25}ClN_4O_3S+H$). Anal. Found for $C_{26}H_{25}ClN_4O_3S$: C, 60.89; H, 5.03; N, 10.81; Cl, 7.04; S, 6.30.

All cited publications, patents, and patent documents (including the full text of U.S. Provisional Application No. 60/123660, from which this application claims priority) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula L-3:

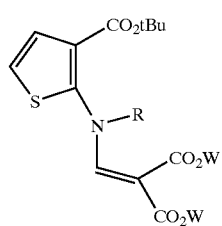

wherein R is $C_{1-4}$ alkyl, and each W is independently selected from $C_{1-4}$ alkyl.

2. A compound of formula L-4:

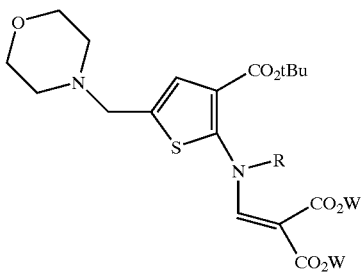

wherein R is $C_{1-4}$ alkyl, and each W is independently selected from $C_{1-4}$ alkyl.

3. A compound of formula L-5:

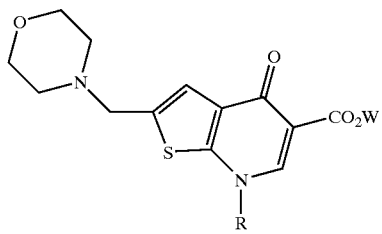

wherein R is $C_{1-4}$ alkyl, and W is H or $C_{1-4}$ alkyl.

4. The compound of claim 1, 2, or 3 wherein R is methyl and W is ethyl.

5. The compound of claim 1, wherein R is methyl and W is ethyl.

6. The compound of claim 2, wherein R is methyl and W is ethyl.

7. The compound of claim 3, wherein R is methyl and W is ethyl.

8. The compound:

(1) N-(3-tert-butoxycarbonyl-thien-2-yl)-N-methylaminomethylenemalonic acid diethyl ester;

(2) N-(3-tert-butoxycarbonyl-5 morpholinomethyl-thien-2-yl)-N-methylaminomethylenemalonic acid diethyl ester;

(3) ethyl 7-methyl-2-(4-morpholinomethyl)-4-oxo-4,7-dihydrothieno[2,3-b]pyridine-5-carboxylate; or (4) 7-methyl-2-(4-morpholinomethyl)-4-oxo-4,7-dihydrothieno[2,3-b]pyridine-5-carboxylic acid.

* * * * *

UNITED STATES PATENT AND TRADEMARK OFFICE
CERTIFICATE OF CORRECTION

PATENT NO. : 6,495,683 B2  Page 1 of 1
DATED : December 17, 2002
INVENTOR(S) : Allen Scott It is certified that error appears in the above-identified patent and that said Letters Patent is hereby corrected as shown below:

Title page, Item [54] and Column 1, lines 3-5,
Delete "4-OXO-4,7-DIHYDRO-THIENO[2,3-B] PYRIDINE-5-CARBOXAMIDES AS ANTIVIRAL AGENTS" and insert -- 4-OXO-4,7-DIHYDRO-THIENO[2,3-b] PYRIDINE-5-CARBOXAMIDES AS ANTIVIRAL AGENTS --, therefor.

Title page,
Item [56], "FOREIGN PATENT DOCUMENTS, 2nd reference, insert
-- C07D/495.04 -- after "2/1991".

Signed and Sealed this

Twenty-second Day of July, 2003

JAMES E. ROGAN
*Director of the United States Patent and Trademark Office*